(12) United States Patent
Sard et al.

(10) Patent No.: US 8,071,786 B2
(45) Date of Patent: Dec. 6, 2011

(54) INDOLE COMPOUNDS USEFUL AS SEROTONIN SELECTIVE AGENTS

(75) Inventors: Howard P. Sard, Arlington, MA (US); Louis Shuster, Brighton, MA (US); Bryan Roth, Moreland Hills, OH (US); Cynthia Morency, Andover, MA (US); Govindaraj Kumaran, Woburn, MA (US); Liang Xu, Woburn, MA (US)

(73) Assignee: Galenea Corp., Cambridge, MA (US)

( * ) Notice: Subject to any disclaimer, the term of this patent is extended or adjusted under 35 U.S.C. 154(b) by 0 days.

(21) Appl. No.: 12/637,600

(22) Filed: Dec. 14, 2009

(65) Prior Publication Data

US 2010/0137616 A1      Jun. 3, 2010

Related U.S. Application Data

(63) Continuation of application No. 11/237,318, filed on Sep. 27, 2005, now Pat. No. 7,655,691.

(51) Int. Cl.
*C07D 209/14*      (2006.01)
(52) U.S. Cl. ..................................................... 548/506
(58) Field of Classification Search .................. 548/506
See application file for complete search history.

(56) References Cited

U.S. PATENT DOCUMENTS

| 3,075,992 A | 1/1963 | Hofmann et al. | |
|---|---|---|---|
| 2009/0318527 A1* | 12/2009 | Sard et al. | 514/415 |

FOREIGN PATENT DOCUMENTS

| WO | 9005721 | 5/1990 |
|---|---|---|
| WO | 0012482 | 3/2000 |

OTHER PUBLICATIONS

International Search Report from corresponding international patent application No. PCT/US2005/034413, dated May 8, 2009.
Blair et al., "Effect of Ring Fluorination on the Pharmacology of Hallucinogenic Tryptamines." Journal of Medicinal Chemistry (2000) p. 4701-4710 August.
Cerletti et al., Advances in Pharmacology (New York) (1968), 6 (Pt. B), 233-46.
Vippagunta et al., Advanced Drug Delivery Reviews 48 (2001) pp. 3-26.
Audia et al., "Potent, Selective Tetrahydro-b-carboline Antagonists of the Serotonin 2B (5HT 2B) Contractile Receptor in the Rat Stomach Fundus," J. Med. Chem. (1996), vol. 39, pp. 2773-2780.
Bickerdike et al.,"5-HT2C Receptor Modulation and the Treatment of Obesity," Diabetes Obes. Metab. 1999, vol. 1, pp. 207-214.
Blakeslee, "Scientists Test Hallucinogens for Mental IIIs," New York Times, Mar. 31 2001, 4 pages.
Bös et al., "Novel Agonists of 5-HT2C Receptors. Synthesis and Biological Evaluation of Substituted 2-(Indo1-1-yl)-1-methylethylamines and 2-(Indeno[1,2-b]pyrrol-1-yl)-1-methylethylamines. Improved Therapeutics for Obsessive Compulsive Disorder," J. Med. Chem. 1997, 40, 2762-2769.
Brodey et al., abstract of "An electrographic study of psilocin and 4-methyl-a'-methyl-tryptamine," J. Pharm. & Exp. Ther. (1963), vol. 140, pp. 8-18.
Cliffe et al., "Approaches to 5-HT2C Receptor Agonists: Activity of Saturated Cycloalkyl-fused [b]indole and [b] indole isotryptamines," Excellence in Neuroscience and CNS Medicine, 224th ACS National Meeting, Aug. 18-22, 2002, Boston (6 pages).
Delgado et al., "Hallucinogens, Serotonin, and Obsessive-Compulsive Disorder," J. Psychoactive Drugs (Oct.-Dec. 1998), vol. 30(4), pp. 359-366.
Fitzgerald et al., "5-HT2C Receptor Modulators; Progress in Development of New CNS Medicines," Annual Reports in Medicinal Chemistry(2002), vol. 37, pp. 21-30.
Fitzgerald et al., "Possible Role of Valvular Serotonin 5-HT2B Receptors in the Cardiopathy Associated with Fenfluramine," Molecular Pharmacology (2000), vol. 57, pp. 75-81.
Glennon et al., "Influence of Amine Substituents of 5-HT2A Versus 5HT2C Binding of Phenylalkyl- and Indolylalkylamines," J. Med. Chem. (1994), vol. 37, pp. 1929-1935.
Goodman, W. K., "Obsessive-Compulsive Disorder: Diagnosis and Treatment," J. Clin. Psychiatry (1999), vol. 60 (Suppl. 18), pp. 27-32.
Jacob et al., "Structure-Activity Relationships of the Classic Hallucinogens and Their Analogs," NIDA Research Monograph 146 (Hallucinogens, an Update), Eds. Lin, G.C. And Glennon, R.A. (1994), pp. 74-91.
Martin et al., " 5-HT2C Receptor Agonists: Pharmacological Characteristics and Therapeutics Potential," Journal of Pharmacology and Experimental Therapeutics, (1998), vol. 285, pp. 913-924.
Moreno et al., "Hallucinogen-Induced Relief of Obsessions and Compulsions," Am. J. Psychiatry (1997), vol. 154. pp. 1037-1038.
Perrine, D. M. "Hallucinogens and Obsessive-Compulsive Disorder," Am. J. Psychiatry (1999), vol. 156, pp. 1123.
Roth et al., "Insights into the Structure and Function of 5-HT2 Family Serotonin Receptors Reveal Novel Strategies for Therapeutic Target Development," Expert Opin. Ther. Targets (2001), vol. 5(6), pp. 685-695.
Rothman, et al., "Evidence for Possible Involvement of 5-HT2B Receptors in the Cardiac Valvulopathy Associated with Fenfluramine and Other Serotonergic Medications," Circulation (2000), vol. 102, pp. 2836-2841.
Smith et al., "Discovery and SAR of New benzazepines as potent and selective 5-HT2C Receptor Agonists for the Treatment of Obesity," Bioorganic & Medicinal Chemistry Letters (2005), vol. 15. pp. 1467-1470.
Tecott et al., "Eating Disorder and Epilepsy in Mice lacking 5-HT2C Serotonin Receptors", Nature (Apr. 6, 1995), vol. 374, pp. 542-546.
Uckert et al., "Current and Future Trends in the Oral Pharmacotherapy of Male Erectile Dysfunction," Expert Opin. Investig. Drugs (2003), vol. 12(9), pp. 1521-1533.
Welmaker et al., "Synthesis and 5-Hydroxytryptamine (5-HT) Activity of 2,3,4,4a-Tetrahydro-1H-Pyrazinol[1,2-a] quinoxalin-5-(6H)ones and 2,3,4a,5,6-Hexahydro-1H-pyrazinol[1,2-a] quinoxalines," Bioorganic & Medicinal Chemistry Letters (2000), vol. 10, pp. 1991-1994.

(Continued)

*Primary Examiner* — Shawquia Young
(74) *Attorney, Agent, or Firm* — Lando & Anastasi LLP

(57) ABSTRACT

Novel indole compounds are disclosed. Also disclosed are methods for using the compounds to treat human and animal disease, pharmaceutical compositions of the compounds, and kits including the compounds.

19 Claims, 1 Drawing Sheet

OTHER PUBLICATIONS

International Search Report and Written Opinion for International Application No. PCT/US05/34413 (11 pages), 2006.

Cecil Textbook of Medicine, 20th Edition (1996), vol. 2, pp. 2050-2057.

Cecil Textbook of Medicine, 20th Edition (1996), vol. 2, pp. 1992-1996.

FDA Mulls Drug to slow late-stage Alzheimer's [online], [retrieved on Sep. 23, 2003]. Retrieved from the internet, URL; http://www.cnn.com/2003/HEALTH/conditions/09/24/alzheimers.drug.ap/indexhtml>.

Autism[online], [retrieved on Dec. 5, 2006]. Retrieved from the internet, URL; http://en.wikipedia.org/wiki/autism>.

Whitaker-Azmitia, P., "Behavioral and Cellular Consequences of Increasing Serotonergic Activity During Brain Development: A Role in Autism?" Int. J. Devl. Neuroscience (2005), vol. 23, pp. 75-83.

Acral lick Dermatitis (Lick Granuloma)[online], [retrieved on Aug. 29, 2007], Retrieved from the internet, URL; http://www.animalhealthcare.com/handouts/dogs/acrall1.htm>.

* cited by examiner

INDOLE COMPOUNDS USEFUL AS SEROTONIN SELECTIVE AGENTS

CROSS-REFERENCE TO RELATED APPLICATIONS

This application is a continuation of U.S. patent application Ser. No. 11/237,318, filed Sep. 27, 2005, which claims the benefit of U.S. Provisional Patent Application No. 60/613,944, filed Sep. 27, 2004, the contents of each of which are incorporated herein by reference in their entirety.

STATEMENT OF GOVERNMENT INTEREST

The invention was made at least in part with National Institutes of Health grants #1-R43-MH63529-01-A1 and #5-R43-DK065322-02. The U.S. Government may have certain rights in the invention.

FIELD OF THE INVENTION

This invention relates to novel indole compounds, and their use as selective agents at serotonin receptors.

BACKGROUND OF THE INVENTION

Serotonin (5-hydroxytryptamine, 5-HT) plays a significant role in influencing a large number of central and peripheral processes. 5-HT-selective pharmacotherapies have been developed to treat a wide variety of medical problems including depression, anxiety, schizophrenia, migraine, emesis, and appetite control (Annual Reports in Medicinal Chemistry, Volume 32, 2002, Academic Press, Fitzgerald, L., Ennis, M. "5-HT$_{2C}$ Receptor Modulators: Progress in Development of New CNS Medicines" pp 21-30). 5-HT exerts its influence through activation of fourteen distinct receptor subtypes in seven separate families. There is particular interest in the three receptor subtypes of the 5-HT$_2$ family, 5-HT$_{2A}$, 5-HT$_{2B}$, and 5-HT$_{2C}$. Modulation of the 5-HT$_{2C}$ receptor subtype has been shown to play a role in numerous human diseases including obesity, obsessive-compulsive disorder (OCD), sexual dysfunction, epilepsy, schizophrenia, and anxiety disorders (Roth, B., Shapiro, D. "Insights into the Structure and Function of 5-HT2 Family Serotonin Receptors Reveal Novel Strategies for Therapeutic Target Development" *Expert Opin. Ther. Targets* 2001, 5, 685; Martin, J., Bos, M., Jenck, F., Moreau, J-I., Mutel, V., Sleight, A., Wichmann, J., Andrews, J., Berendsen, H., Broekkamp, C., Ruight, G., Kohler, C., van Delft, A. "5-HT$_{2C}$ Receptor Agonists: Pharmacological Characteristics and Therapeutic Potential" *J. Pharm. Experimental Ther.* 1998, 286, 913). However, the transmembrane sequence homology between the 5-HT$_{2C}$ receptor and the 5-HT$_{2A}$ and 5-HT$_{2B}$ receptors is high (Bickerdike, M., Vickers, S., Dourish, C. "5-HT$_{2C}$ Receptor Modulation and the Treatment of Obesity" *Diabetes Obes. Metab.* 1999, 1, 207; Glennon, R., Dukat, M., El-Bermawy, M., Law, H., De Los Angeles, J., Teitler, M., King, A., Herrick-Davis, K. "Influence of Amine Substituents on 5-HT$_{2A}$ versus 5-HT$_{2C}$ Binding of Phenylalkyl- and Indolylalkylamines" *J. Med. Chem.* 1994, 37, 1929). Thus selectivity for the 5-HT$_{2C}$ receptor can be difficult to obtain, however such selectivity is important from a drug development standpoint. 5-HT$_{2B}$ receptor agonists are associated with heart valve toxicity (Rothman, R., Baumann, M., Savage, J., Rauser, L., McBride, A., Hufeisen, S., Roth, B. L. "Evidence for Possible Involvement of 5-HT$_{2B}$ Receptors in the Cardiac Valvulopathy Associated with Fenfluramine and other Serotonergic Medications" *Circulation* 2000, 102, 2836; Fitzgerald, L., Burn, T., Brown, B., Patterson, J., Corjay, M., Valentine, P., Sun, J-H., Link, J., Abbaszade, I., Hollis, J., Largent, B., Hartig, P., Hollis, G., Meunier, P., Robichaud, A., Robertson, D. "Possible Role of Valvular Serotonin 5-HT$_{2B}$ Receptors in the Cardiopathy Associated with Fenfluramine" *Molecular Pharmacology* 2000, 57, 75) and pulmonary hypertension (Launay, J., Herve, P., Peoc'h, K., Tournois, C., Callebert, J., Nebigil, C., Etienne, N., Drouet, L., Humbert, M., Simonneau, G., Maroteaux, L. "Function of the Serotonin 5-Hydroxytryptamine 2B Receptor in Pulmonary Hypertension" *Nat. Med.* 2002, 8, 1129). However, the 5-HT$_{2C}$ receptor is found only in the CNS (Bickerdike, M., Vickers, S., Dourish, C. "5-HT$_{2C}$ Receptor Modulation and the Treatment of Obesity" *Diabetes Obes. Metab.* 1999, 1, 207; Martin, J., Bos, M., Jenck, F., Moreau, J-I., Mutel, V., Sleight, A., Wichmann, J., Andrews, J., Berendsen, H., Broekkamp, C., Ruight, G., Kohler, C., van Delft, A. "5-HT$_{2C}$ Receptor Agonists: Pharmacological Characteristics and Therapeutic Potential" *J. Pharm. Experimental Ther.* 1998, 286, 913), and agonists that discriminate for 5-HT$_{2C}$ over 5-HT$_{2B}$ should not display cardio- or pulmonary toxicity. Selectivitiy for 5-HT$_{2C}$ over 5-HT$_{2A}$ receptors is also important since agonists at 5-HT$_{2A}$ generally display undesirable hallucinogenic activity (e.g. LSD, psilocybin).

Psilocybin (4-phosphoryloxy-N,N-dimethyltryptamine) is an agonist at the 5-HT$_{2A}$ and 5-HT$_{2C}$ receptors. Its binding potency at 5-HT$_{2A}$ correlates with its activity as a hallucinogen in humans (Delgado, P. L., Moreno, F. A. "Hallucinogens, Serotonin, and Obsessive-Compulsive Disorder" *J. Psychoactive Drugs* 1998, 30, 359; Perrin, D. M. "Hallucinogens and Obsessive-Compulsive Disorder" *Am. J. Psychiatry* 1999, 156, 1123; Moreno, F. A., Delgado, P. L. "Hallucinogen-Induced Relief of Obsessions and Compulsions" *Am. J. Psychiatry* 1997, 154, 1037). More than 40 years ago, some derivatives of psilocybin were reported by workers at Sandoz (Hofmann, A., Troxler, F. U.S. Pat. No. 3,075,992; U.S. Pat. No. 3,078,214). This work was carried out prior to the ability to test for activity at specific serotonin receptor subtypes. More recently, considerable effort has been made in seeking selective 5-HT$_{2C}$ receptor ligands. The indole Ro 60-0175 (Martin, J., Bos, M., Jenck, F., Moreau, J-I., Mutel, V., Sleight, A., Wichmann, J., Andrews, J., Berendsen, H., Broekkamp, C., Ruight, G., Kohler, C., van Delft, A. "5-HT$_{2C}$ Receptor Agonists: Pharmacological Characteristics and Therapeutic Potential" *J. Pharm. Experimental Ther.* 1998, 286, 913; Bos, M., Jenck, F., Martin, J., Moreau, J-I., Sleight, A., Wichmann, J., Widmer, U. "Novel Agonists of 5-HT$_{2C}$ Receptors. Synthesis and Biological Evaluation of Substituted 2-(Indol-1-yl)-1-methylethylamines and 2-(Indeno[1,2-b]pyrrol-1-methylethylamines Improved Therapeutics for Obsessive Compulsive Disorder" *J. Med. Chem.* 1997, 45, 2762) is 25 times more active at 5-HT$_{2C}$ as compared to 5-HT$_{2A}$, however it is not selective over 5-HT$_{2B}$ receptors (Bickerdike, M., Vickers, S., Dourish, C. "5-HT$_{2C}$ Receptor Modulation and the Treatment of Obesity" *Diabetes Obes. Metab.* 1999, 1, 207). Certain 1-methyl-5-substituted indoles reported by Lilly are selective 5-HT$_{2B}$ antagonists (Audia, J., Evrard, D., Murdoch, G., Droste, J., Nissen, J., Schenck, K., Fludzinski, Z., Lucaites, V., Nelson, D., Cohen, M. "Potent, Selective Tetrahydro-β-carboline Antagonists of the Serotonin 2B (5HT$_{2B}$) Contractile Receptor in the Rat Stomach Fundus" *J. Med. Chem.* 1996, 39, 2773). Substituted indoles were reported by Vernalis to be highly selective agonists at 5-HT$_{2C}$ as compared to 5-HT$_{2A}$ (American Chemical Society National Meeting, Boston, Mass., Aug. 18-22, 2002, Poster Session, Division of Medicinal Chemistry, Wednesday morning, August 21, #344-349). Wyeth has reported 5-HT$_{2C}$ agonists including WAY161503 that are active in an animal model of obesity (Welmaker, G., Nelson, A., Sabalski, J., Sabb, A., Potoski, J., Graziano, D., Kagan, M., Coupet, J., Dunlop, J., Mazandarani, H., Rosenzwieg-Lipson, S., Sukoff, S., Zhang, Y. "Synthesis and 5-hydroxytryptamine (5-HT) activity of 2,3,4,4a-tetrahydro-1H-pyrazino[1,2-a]quinoxalin-5-(6H)ones and 2,3,4,4a,5,6-hexahydro-1H-pyrazino[1,2-a]quinoxalines" *Bioorg. Med. Chem. Lett.* 2000, 10, 1991). Yamanouchi has described indazole compounds including YM348 which are 5-HT$_{2C}$ agonists showing activity in an animal model of obesity (Kimura, Y., Hatanaka, K., Naitou, Y., Maeno, K., Shimada, I., Koakutsu, A., Wanibuchi, F., Yamaguchi, T., "Pharmacological profile of YM348, a novel, potent and orally active 5-HT2C receptor agonist" *Eur. J. Pharmacol.* 2004, 483, 37). Arena reports mCPP analogs active in vivo as potential obesity treatments (Smith, B., Smith, J., Tsai, J., Schultz, J., Gilson, C., Estrada, S., Chen, R., Park, D., Prieto, E., Gallardo, C., Sengupta, D., Thomsen, W., Saldana, H., Whelan, K., Menzaghi, F., Webb. R., Beeley, N. "Discovery and SAR of new benzazepines as potent and selective 5-HT(2C) receptor agonists for the treatment of obesity" *Bioorg. Med. Chem. Lett.* 2005, 15, 1467).

Obesity is one of the most important health problems currently affecting the U.S. population. The overweight suffer a significantly higher death rate, as well as a much greater risk of developing many diseases including type 2 diabetes, sleep apnea, hypertension, osteoarthritis, and some forms of cancer. Exercise and diet modification allow some obese people to lose weight. However, many others are unable to achieve lasting weight loss by such methods, and pharmaceutical agents that promote satiety can be effective and appropriate treatments.

Considerable evidence has accumulated implicating 5-HT$_{2C}$ receptor activation with appetite suppression. In 1995, transgenic mice lacking the 5-HT$_{2C}$ receptor were shown to become obese (Tecott, L., Sun, L., Akana, S., Strack, A., Lowenstein, D., Dallman, M., Julius, D. "Eating Disorder and Epilepsy in Mice Lacking 5-HT$_{2C}$ Serotonin Receptors" *Nature* 1995, 374, 542). A clinical study in 1997 (Sargent, P., Sharpley, A., Williams, C., Cowen, P. "5-HT$_{2C}$-Receptor Activation Decreases Appetite and Body Weight in Obese Subjects" *Psychopharmacology* 1997, 133, 309) using meta-chlorophenylpiperazine (mCPP), a 5-HT$_{2C}$ agonist, has shown appetite reduction and weight loss in obese subjects. Furthermore, selective 5-HT$_{2C}$ antagonists reduce or eliminate the anorexic effects of 5-HT$_{2C}$ agonists (Kennett, G., Wood, M., Bright, F., Trail, B., Riley, G., Holland, K., Avenell, K., Stean, T., Upton, N., Bromidge, S., Forbes, I., Middlemiss, D., Blackburn, T. "SB242082, a Selective and Brain Penetrant 5-HT$_{2C}$ Receptor Antagonist" *Neuropharmacology,* 1997, 36, 609). Fenfluramine is a non-selective 5-HT$_{2C}$ receptor agonist which together with phenteramine ("phen-fen") was marketed until recently as a highly effective appetite suppressant. The clinical effectiveness of fenfluramine as an appetite suppressant has been shown to be largely due to its activity as a 5-HT$_{2C}$ receptor agonist (Bickerdike, M., Vickers, S., Dourish, C. "5-HT$_{2C}$ Receptor Modulation and the Treatment of Obesity" *Diabetes Obes. Metab.* 1999, 1, 207; Vickers, S., Dourish, C., Kennett, G. "Evidence that Hypophagia Induced by d-Fenfluramine and d-Norfenfluramine in the Rat is Mediated by 5-HT$_{2C}$ Receptors" *Neuropharmacology* 2001, 41, 200).

Obsessive Compulsive Disorder (OCD) is a mental illness involving persistent and distressing thoughts and actions that significantly interfere with normal life. OCD afflicts at least 1-2% of the population in the US and worldwide, and is the fourth most common psychiatric diagnosis in the United States (Delgado, P. L., Moreno, F. A. "Hallucinogens, Serotonin, and Obsessive-Compulsive Disorder" *J. Psychoactive Drugs* 1998, 30, 359; Goodman, W. K. "Obsessive-Compulsive Disorder: Diagnosis and Treatment" *J. Clin. Psychiatry* 1999, 60 (Suppl 18), 27). OCD is currently treated pharmacologically and/or with psychotherapy. Current pharmacotherapy for OCD has significant limitations and the discovery of an improved medication for OCD would have considerable commercial potential.

Psilocybin, a 5-HT$_{2C}$ receptor agonist, is currently in a Phase I clinical trial with OCD patients (The New York Times, Page D1, Mar. 13, 2001). Other 5-HT$_{2C}$ receptor agonists are recognized as potential treatments for OCD (Martin, J., Bos, M., Jenck, F., Moreau, J-I., Mutel, V., Sleight, A., Wichmann, J., Andrews, J., Berendsen, H., Broekkamp, C., Ruight, G., Kohler, C., van Delft, A. "5-HT$_{2C}$ Receptor Agonists: Pharmacological Characteristics and Therapeutic Potential" *J. Pharm. Experimental Ther.* 1998, 286, 913).

Other possible uses for 5-HT$_{2C}$ selective compounds include treatments for epilepsy (Isaac, M. "Serotonergic 5-HT2C Receptors as a Potential Therapeutic Target for the Design Antiepileptic Drugs" *Current Topics in Medicinal Chemistry,* 2005, 5, 59), Alzheimer's disease (Arjona, A., Pooler, A., Lee, R., Wurtman, R. "Effect of a 5-HT(2C) Serotonin Agonist, Dexnorfenfluramine, on Amyloid Precursor Protein Metabolism in Guinea Pigs" *Brain Res.* 2002, 951, 135), sexual dysfunction (Uckert, S., Stief, C., Jonas, U. "Current and Future Trends in the Oral Pharmacotherapy of Male Erectile Dysfunction" *Expert Opin. Investig. Drugs* 2003, 12, 1521; Millan, M., Peglion, J., Lavielle, G., Perrin-Monneyron, S. "5-HT2C Receptors Mediate Penile Erections in Rats: Actions of Novel and Selective Agonists and Antagonists" *Eur. J. Pharmacol.* 1997, 325, 9), and substance abuse and addiction disorders (Kampman, K., Pettinata, H., Lynch, K., Sparkman, T., O'Brien, C "A Pilot Trial of Olanzapine for Cocaine Dependence" *Drug Alcohol Depend.* 2003, 70, 265).

Compounds that are selective for the 5-HT$_{2C}$ receptor may therefore have therapeutic potential in treating, for example, the above disorders. Such selectivity can also reduce possible side effects due to activity at other serotonin receptors.

Certain N-unsubstituted psilocin derivatives containing fluorine substitution at the 5-, 6-, or 7-position have been reported (Blair, J., Kurrasch-Orbaugh, D., Marona-Lewicka, D., Cumbay, M., Watts, V., Barker, E., Nichols, D. "Effect of Fluorine Substitution on the Pharmacology of Hallucinogenic Tryptamines" *J. Med. Chem.* 2000, 43, 4701), and some of these compounds were shown to have reduced activity at the 5-HT$_{2A}$ receptor as compared to psilocin itself.

SUMMARY OF THE INVENTION

The present invention relates to novel N-substituted psilocin (4-hydroxyindole) derivatives that are also substituted at the 5-, 6-, and/or 7-positions and possess 5-HT$_{2C}$ receptor selectivity, preferably versus both the 5HT$_{2A}$ and 5-HT$_{2B}$ receptors. Such compounds have not previously been described or recognized to have selective functional activity at the 5-HT$_{2C}$-receptor or to have in vivo activity in an animal model of human disease.

The invention also relates to N-substituted psilocybin (4-phosphoryloxyindole) derivatives, also substituted at the 5-, 6-, and/or 7-positions. Without wishing to be bound by theory, it is believed that such compounds act as prodrugs for the corresponding 4-hydroxy compounds in vivo (Jacob III, P.; Shulgin, A. T. in *NIDA Research Monograph* 146 (*Hallucinogens, an Update*), 2000, Eds. Lin, G. C.; Glennon, R. A., pp 74).

In one aspect, the invention provides a compound represented by the structural formula:

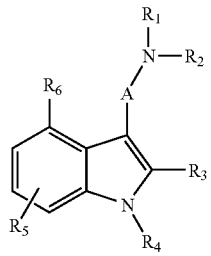

(Formula I)

in which A is $C_1$-$C_4$ alkylene, $C_2$-$C_4$ alkenylene, or $C_2$-C4 alkynylene;

$R_1$ and $R_2$ are, independently for each occurrence, H, $C_1$-$C_8$ alkyl, $C_2$-$C_8$ alkenyl, or $C_2$-$C_8$ alkynyl;

$R_3$ is hydrogen, $C_1$-$C_8$ alkyl, $C_2$-$C_8$ alkenyl, or $C_2$-$C_8$ alkynyl, optionally substituted with 1-3 substitutents selected from the group consisting of halogen, cyano, hydroxy, $C_1$-$C_8$ alkoxyl, —SH, $C_1$-$C_8$ thioalkyl, amino, $C_1$-$C_8$ alkylamino, di($C_1$-$C_8$ alkyl)amino, $C_1$-$C_8$ alkylsulfonyl, formyl, and COOH; or $R_3$ is selected from the group consisting of halogen, $C_1$-$C_8$ alkylsulfonyl, formyl, COOH, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

$R_4$ is $C_1$-$C_8$ alkyl, $C_2$-$C_8$ alkenyl, or $C_2$-$C_8$ alkynyl, optionally substituted with 1-3 substituents selected from the group consisting of halogen, cyano, hydroxy, $C_1$-$C_8$ alkoxyl, —SH, $C_1$-$C_8$ thioalkyl, amino, $C_1$-$C_8$ alkylamino, di($C_1$-$C_8$ alkyl)amino, $C_1$-$C_8$ alkylsulfonyl, formyl, and COOH; or $R_4$ is selected from the group consisting of $C_1$-$C_8$ alkylsulfonyl, formyl, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

$R_5$ represents 1-3 substituents selected from the group consisting of $C_1$-$C_8$ alkyl, $C_2$-$C_8$ alkenyl, and $C_2$-$C_8$ alkynyl, each optionally substituted with 1-3 substitutents selected from the group consisting of halogen, cyano, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino; or $R_5$ represents 1-3 substituents selected from the group consisting of halogen, $C_1$-$C_8$ alkylsulfonyl, formyl, COOH, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

$R_6$ is OP(O)(OH)$_2$, OH, OC(O)$R_7$, OSO$_2$OH, or SO$_2$NH$_2$;

$R_7$ is $C_1$-$C_8$ alkyl or phenyl;

or a pharmaceutically acceptable salt, solvate, ester, or pro-drug thereof.

In another aspect, the invention provides a compound represented by the structural formula:

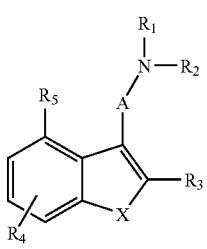

(Formula II)

in which A is $C_1$-$C_4$ alkylene, $C_2$-$C_4$ alkenylene, or $C_2$-C4 alkynylene;

X is S, SO, SO$_2$, or O;

$R_1$ and $R_2$ are, independently for each occurrence, H, $C_1$-$C_8$ alkyl, $C_2$-$C_8$ alkenyl, or $C_2$-$C_8$ alkynyl;

$R_3$ is hydrogen, $C_1$-$C_8$ alkyl, $C_2$-$C_8$ alkenyl, or $C_2$-$C_8$ alkynyl, optionally substituted with 1-3 substitutents selected from the group consisting of halogen, cyano, hydroxy, $C_1$-$C_8$ alkoxyl, —SH, $C_1$-$C_8$ thioalkyl, amino, $C_1$-$C_8$ alkylamino, di($C_1$-$C_8$ alkyl)amino, $C_1$-$C_8$ alkylsulfonyl, formyl, and COOH; or $R_3$ is selected from the group consisting of halogen, $C_1$-$C_8$ alkylsulfonyl, formyl, COOH, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

$R_4$ represents 1-3 substituents selected from the group consisting of $C_1$-$C_8$ alkyl, $C_2$-$C_8$ alkenyl, and $C_2$-$C_8$ alkynyl, each optionally substituted with 1-3 substitutents selected from the group consisting of halogen, cyano, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino; or $R_4$ represents 1-3 substituents selected from the group consisting of halogen, $C_1$-$C_8$ alkylsulfonyl, formyl, COOH, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

$R_5$ is OP(O)(OH)$_2$, OH, OC(O)$R_6$, OSO$_2$OH, or SO$_2$NH$_2$; and $R_6$ is $C_1$-$C_8$ alkyl or phenyl;

or a pharmaceutically acceptable salt, solvate, ester, or pro-drug thereof.

In another aspect, the invention provides a method for the treatment of Obsessive Compulsive Disorder (OCD) in a subject. The method includes administering to the subject a compound of Formula I or Formula II, such that OCD is treated.

In another aspect, the invention provides a method for suppressing appetite in a subject The method includes administering to the subject a compound of Formula I or Formula II, such that appetite is suppressed in the subject.

In another aspect, the invention provides a compound represented by the formula:

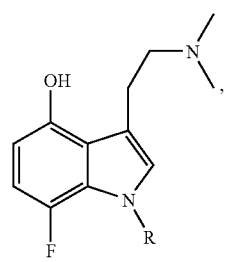

(Formula III)

in which R is $C_1$-$C_8$ alkyl;

or a pharmaceutically acceptable salt, solvate, ester, or pro-drug thereof. In preferred embodiments, R is CH$_3$ or CH$_2$CH$_2$CH$_3$.

In still another aspect, the invention provides a method for the treatment of Obsessive Compulsive Disorder (OCD) in a subject. The method includes administering to the subject a compound of Formula III, such that OCD is treated.

In yet another aspect, the invention provides a method for suppressing appetite in a subject. The method includes administering to the subject a compound of Formula III, such that appetite is suppressed in the subject.

In another aspect, the invention provides a compound represented by the formula:

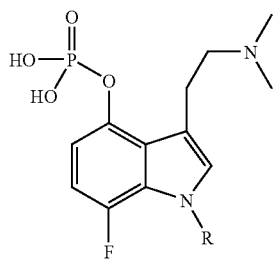

(Formula IV)

in which R is $C_1$-$C_8$ alkyl; or a pharmaceutically acceptable salt, solvate, ester, or pro-drug thereof. In preferred embodiments, R is $CH_3$ or $CH_2CH_2CH_3$.

In still another aspect, the invention provides a method for the treatment of Obsessive Compulsive Disorder (OCD) in a subject. The method includes administering to the subject a compound of Formula IV, such that OCD is treated.

In yet another aspect, the invention provides a method for suppressing appetite in a subject. The method includes administering to the subject a compound of Formula IV, such that appetite is suppressed in the subject.

In still another aspect, the invention provides a method for the treatment of a central nervous system disorder in a subject. The method includes administering to the subject a compound of any one of the formulae herein (e.g., Formulae I-IV), such that the central nervous system disorder is treated. In preferred embodiments, the central nervous system disorder is selected from the group consisting of epilepsy, Alzheimer's disease, sexual dysfunction, addiction, anorexia nervosa, Tourette's syndrome, and trichotillomania.

In still another aspect, the invention provides a method for the treatment of a canine veterinary disease. The method includes administering to the subject a compound of any one of the formulae herein (e.g., Formulae I-IV), such that the canine veterinary disease is treated. In preferred embodiments, the canine veterinary disease is acral lick dermatitis (ALD).

In another aspect, the invention provides a method of increasing the activity of a serotonin receptor, the method comprising contacting a serotonin receptor with a compound of any one of the formulae herein (e.g., Formulae I-IV).

In still further aspects, the invention provides use of a compound of any of the formulae herein (e.g., Formulae I-IV) for the treatment of Obsessive Compulsive Disorder (OCD) in a subject; use of a compound of any of the formulae herein (e.g., Formulae I-IV) for the treatment of obesity and/or suppression of appetite in a subject; use of a compound of any of the formulae herein (e.g., Formulae I-IV) for the preparation of a medicament for treatment of Obsessive Compulsive Disorder (OCD) in a subject; use of a compound of any of the formulae herein (e.g., Formulae I-IV) for the preparation of a medicament for the treatment of obesity and/or suppression of appetite in a subject; and use of a compound for the preparation of a medicament for the treatment of a central nervous system disorder in a subject (in preferred embodiments, the central nervous system disorder is selected from the group consisting of epilepsy, Alzheimer's disease, sexual dysfunction, addiction, anorexia nervosa, Tourette's syndrome, and trichotillomania).

Other advantages, aspects, and embodiments of the invention will be apparent in light of the description herein.

DETAILED DESCRIPTION OF THE INVENTION

1. Definitions

Figure 1:
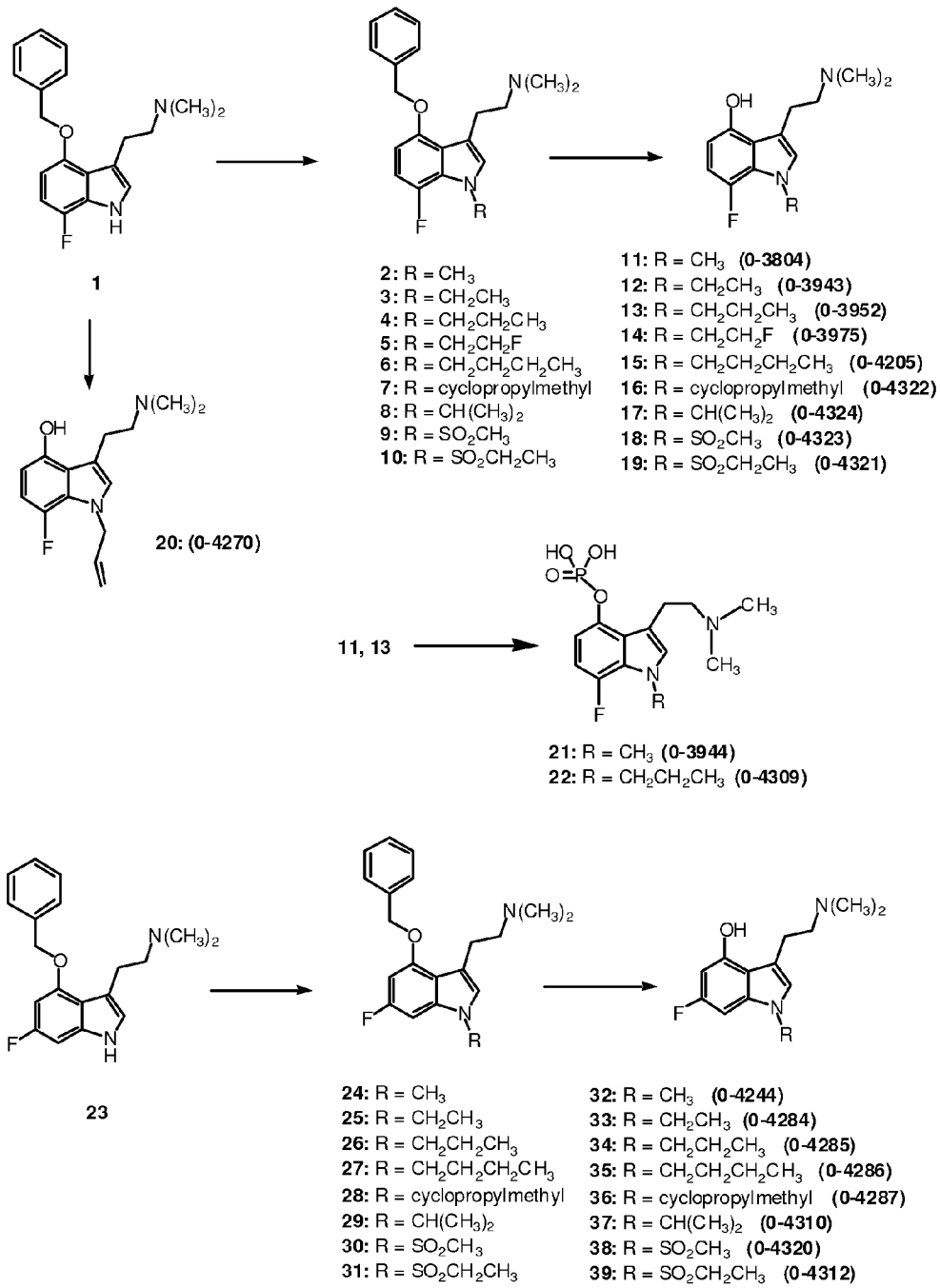
FIG. 1 shows the structures of, and exemplary synthetic routes for preparation of certain compounds of the invention.

Before further description of the present invention, and in order that the invention may be more readily understood, certain terms are first defined and collected here for convenience.

The term "administration" or "administering" includes routes of introducing the compound(s) of the invention to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl(benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., $C_1$-$C_4$ alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The terms "alkylene", "alkenylene" and "alkynylene" refer to divalent aliphatic radicals corresponding respectively to alkyl, alkenyl, and alkynyl groups as defined above, and which may be substituted as described above.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The language "biological activities" of a compound of the invention includes all activities elicited by compound of the inventions in a responsive subject or cell. It includes genomic and non-genomic activities elicited by these compounds.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a subject suffering from OCD, epilepsy, Alzheimer's disease, sexual dysfunction, addiction, anorexia nervosa, Tourette's syndrome, trichotillomania, or other central nervous system disorders, or canine veterinary diseases including acral lick dermatitis (ALD); or an amount effective to suppress appetite in a subject in need of such treatment. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 50 mg/kg body weight, preferably about 0.01 to 40 mg/kg body weight, more preferably about 0.1 to 35 mg/kg body weight, still more preferably about 1 to 30 mg/kg, and even more preferably about 10 to 30 mg/kg. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, halo$C_1$-$C_8$alkyl, halo$C_1$-$C_8$alkoxy, $C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di(C1-C8alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substitutents).

The term "isomers" or "stereoisomers" refers to compounds which have identical chemical constitution, but differ with regard to the arrangement of the atoms or groups in space.

The term "modulate" refers to an increase or decrease, e.g., in the activity of a serotonin receptor in response to exposure to a compound of the invention, e.g., the stimulation of serotonin receptor activity of at least a sub-population of cells in an animal such that a desired end result is achieved, e.g., a therapeutic result.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a disease or condition.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a serotonin-receptor-related disorder or who could otherwise benefit from the administration of a compound of the invention of the invention, such as human and non-human animals. Preferred humans include human patients suffering from or prone to suffering from a serotonin-related disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

With respect to the nomenclature of a chiral center, terms "R" and "S" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides novel indole compounds. In one embodiment, the invention features a compound represented by the formula (Formula I)

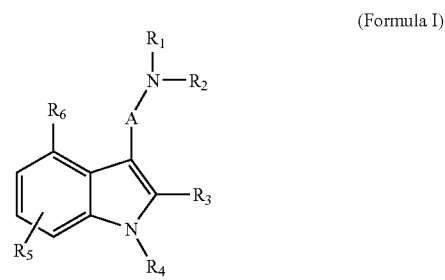

(Formula I)

wherein

A is $C_1$-$C_4$ alkylene, $C_2$-$C_4$ alkenylene, or $C_2$-C4 alkynylene;

$R_1$ and $R_2$ are, independently for each occurrence, H, $C_1$-$C_8$ alkyl, $C_2$-$C_8$ alkenyl, or $C_2$-$C_8$ alkynyl;

$R_3$ is hydrogen, $C_1$-$C_8$ alkyl, $C_2$-$C_8$ alkenyl, or $C_2$-$C_8$ alkynyl, optionally substituted with 1-3 substitutents selected from the group consisting of halogen, cyano, hydroxy, $C_1$-$C_8$ alkoxyl, —SH, $C_1$-$C_8$ thioalkyl, amino, $C_1$-$C_8$ alkylamino, di($C_1$-$C_8$ alkyl)amino, $C_1$-$C_8$ alkylsulfonyl, formyl, and COOH; or $R_3$ is selected from the group consisting of halogen, $C_1$-$C_8$ alkylsulfonyl, formyl, COOH, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino; $R_4$ is $C_1$-$C_8$ alkyl, $C_2$-$C_8$ alkenyl, or $C_2$-$C_8$ alkynyl, optionally substituted with 1-3 substitutents selected from the group consisting of halogen, cyano, hydroxy, $C_1$-$C_8$ alkoxyl, —SH, $C_1$-$C_8$ thioalkyl, amino, $C_1$-$C_8$ alkylamino, di($C_1$-$C_8$ alkyl)amino, $C_1$-$C_8$ alkylsulfonyl, formyl, and COOH; or $R_4$ is selected from the group consisting of $C_1$-$C_8$ alkylsulfonyl, formyl, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

$R_5$ represents 1-3 substituents selected from the group consisting of $C_1$-$C_8$ alkyl, $C_2$-$C_8$ alkenyl, and $C_2$-$C_8$ alkynyl, each optionally substituted with 1-3 substitutents selected from the group consisting of halogen, cyano, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

or $R_5$ represents 1-3 substituents selected from the group consisting of halogen, $C_1$-$C_8$ alkylsulfonyl, formyl, COOH, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

$R_6$ is $OP(O)(OH)_2$, OH, $OC(O)R_7$, $OSO_2OH$, or $SO_2NH_2$;

$R_7$ is $C_1$-$C_8$ alkyl or phenyl;

or a pharmaceutically acceptable salt, solvate, ester, or pro-drug thereof.

In another embodiment, the invention provides a compound represented by the structural formula (Formula II):

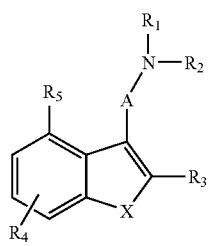

(Formula II)

in which:

A is $C_1$-$C_4$ alkylene, $C_2$-$C_4$ alkenylene, or $C_2$-C4 alkynylene;

X=S, SO, $SO_2$, or O;

$R_1$ and $R_2$ are, independently for each occurrence, H, $C_1$-$C_8$ alkyl, $C_2$-$C_8$ alkenyl, or $C_2$-$C_8$ alkynyl;

$R_3$ is hydrogen, $C_1$-$C_8$ alkyl, $C_2$-$C_8$ alkenyl, or $C_2$-$C_8$ alkynyl, optionally substituted with 1-3 substitutents selected from the group consisting of halogen, cyano, hydroxy, $C_1$-$C_8$ alkoxyl, —SH, $C_1$-$C_8$ thioalkyl, amino, $C_1$-$C_8$ alkylamino, di($C_1$-$C_8$ alkyl)amino, $C_1$-$C_8$ alkylsulfonyl, formyl, and COOH; or $R_3$ is selected from the group consisting of halogen, $C_1$-$C_8$ alkylsulfonyl, formyl, COOH, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

$R_4$ represents 1-3 substituents selected from the group consisting of $C_1$-$C_8$ alkyl, $C_2$-$C_8$ alkenyl, and $C_2$-$C_8$ alkynyl, each optionally substituted with 1-3 substitutents selected from the group consisting of halogen, cyano, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino; or $R_4$ represents 1-3 substituents selected from the group consisting of halogen, $C_1$-$C_8$ alkylsulfonyl, formyl, COOH, hydroxy, $C_1$-$C_8$ alkoxyl, —SH, $C_1$-$C_8$ thioalkyl, amino, $C_1$-$C_8$ alkylamino, and di($C_1$-$C_8$ alkyl)amino;

$R_5$ is $OP(O)(OH)_2$, OH, $OC(O)R_6$, $OSO_2OH$, or $SO_2NH_2$;

$R_6$ is $C_1$-$C_8$ alkyl or phenyl;

or a pharmaceutically acceptable salt, solvate, ester, or pro-drug thereof.

In another embodiment, the invention provides a compound represented by the formula (Formula III):

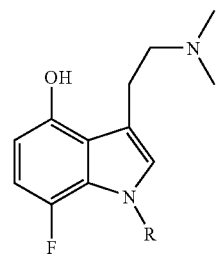

(Formula III)

in which R is alkyl; $CH_3$ or $CH_2CH_2CH_3$; or a pharmaceutically acceptable salt, solvate, ester, or pro-drug thereof. In preferred embodiments, R is selected from $CH_3$ or $CH_2CH_2CH_3$.

In another embodiment, the invention provides a compound represented by the formula (Formula IV):

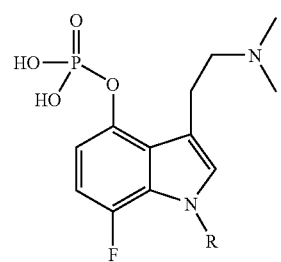

(Formula IV)

wherein R is $CH_3$ or $CH_2CH_2CH_3$;

or a pharmaceutically acceptable salt, solvate, ester, or pro-drug thereof. In preferred embodiments, R is selected from $CH_3$ or $CH_2CH_2CH_3$.

The compounds of the invention can be prepared by a variety of methods, some of which are known in the art or will be apparent to the skilled artisan in light of the present specification. For example, referring to FIG. 1, N-unsubstituted indoles such as compounds 1 and 23 can be N-alkylated or N-sulfonylated, for example, with an alkyl halide or sulfonyl chloride, using a base such as sodium hydride, to give N-alkylated or N-sulfonylated indoles. These 4-substituted indoles can be hydrogenated using, for example, palladium hydroxide on carbon as catalyst in the presence of hydrogen gas, to give 4-hydroxyindoles. The 4-hydroxyindoles can be phosphorylated, for example, by use of tetrabenzylpyrophosphate and a strong base such as lithium diisopropylamide, followed by hydrogenation using, for example, palladium hydroxide on carbon in the presence of hydrogen gas, to give 4-phosphoryloxyindoles.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

3. Uses of the Compounds of the Invention

As described herein below, it has now surprisingly been found that the compounds of the invention have serotonin receptor activity, and can be used to treat or prevent conditions associated with serotonin receptor activity.

Thus, in one embodiment, the invention provides methods for treating a subject for a serotonin-receptor-related disorder, or preventing a serotonin-receptor-related disorder, by administering to the subject an effective amount of a compound of the invention, such that the serotonin-receptor-related disorder is treated or prevented. Serotonin-receptor-related disorders include, e.g., Obsessive Compulsive Disorder (OCD), obesity, epilepsy, Alzheimer's disease, sexual dysfunction, addiction, anorexia nervosa, Tourette's syndrome, and trichotillomania, or other central nervous system disorders, or canine veterinary diseases including acral lick dermatitis (ALD). In certain embodiments, the subject is a mammal, e.g., a primate, e.g., a human.

In one embodiment, a method of treating a subject suffering from or susceptible to a serotonin-receptor-related disorder includes administering to a subject in need thereof a therapeutically effective amount of a compound of the invention, to thereby treat the subject suffering from or susceptible to a serotonin-receptor-related disorder.

A further aspect relates to a method of treating a subject suffering from or susceptible to Obsessive Compulsive Disorder (OCD), including administering to the subject an effective amount of a compound of the invention to thereby treat the subject suffering from or susceptible to OCD.

A further aspect relates to a method of treating a subject suffering from or susceptible to obesity, including administering to the subject an effective amount of a compound of the invention to thereby treat the subject suffering from or susceptible to obesity. In certain embodiments, the methods of the invention include administering to a subject a therapeutically effective amount of a compound of the invention in combination with another pharmaceutically active compound. Examples of pharmaceutically active compounds include compounds known to treat serotonin-related diseases. Other pharmaceutically active compounds that may be used can be found in *Harrison's Principles of Internal Medicine*, Sixteenth Edition, Eds. D. L. Kasper et al. McGraw-Hill Professional, N.Y., N.Y. (2004); and the 2005 Physician's Desk Reference 59th Edition, Thomson Healthcare, 2004, the complete contents of which are expressly incorporated herein by reference. The compound of the invention and the pharmaceutically active compound may be administered to the subject in the same pharmaceutical composition or in different pharmaceutical compositions (at the same time or at different times).

Determination of a therapeutically effective or a prophylactically effective amount of the compound of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective amount or dose, and the prophylactically effective amount or dose, a number of factors are considered by the attending clinician, including, but not limited to: the specific serotonin-receptor-related disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective amount of a compound of the invention of the invention is expected to vary from about 0.1 milligram per kilogram of body weight per day (mg/kg/day) to about 100 mg/kg/day.

Compounds determined to be effective for the prevention or treatment of serotonin-receptor-related disorders in animals, e.g., dogs, chickens, and rodents, may also be useful in treatment of serotonin-receptor-related disorders in humans. Those skilled in the art of treating serotonin-receptor-related disorders in humans will know, based upon the data obtained in animal studies, the dosage and route of administration of the compound to humans. In general, the dosage and route of administration in humans is expected to be similar to that in animals.

The identification of those patients who are in need of prophylactic treatment for serotonin-receptor-related disorders is well within the ability and knowledge of one skilled in the art. Certain of the methods for identification of patients which are at risk of developing serotonin-receptor-related disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

In another aspect, a compound of the invention is packaged in a therapeutically effective amount with a pharmaceutically acceptable carrier or diluent. The composition may be formulated for treating a subject suffering from or susceptible to a serotonin-receptor-related disorder, and packaged with instructions to treat a subject suffering from or susceptible to a serotonin-receptor-related disorder.

In another aspect, the invention provides methods for stimulating or increasing serotonin receptor activity. In one embodiment, a method of increasing serotonin receptor activity (or a serotonin receptor related activity) according to the invention includes contacting cells with a compound capable of increasing serotonin receptor activity. The contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a serotonin-receptor-related disorder in a subject include administering an effective amount of a compound of the invention (e.g., a compound of any of the formulae herein capable of increasing serotonin receptor activity) to the subject. The administration may be by any route of administering known in the pharmaceutical arts. The subject may have a serotonin-receptor-related disorder, may be at risk of developing a serotonin-receptor-related disorder, or may need prophylactic treatment prior to anticipated or unanticipated exposure to a conditions capable of increasing susceptibility to a serotonin-receptor-related disorder.

In one aspect, a method of monitoring the progress of a subject being treated with a serotonin receptor active compound of the invention includes determining the pre-treatment status of the serotonin-receptor-related disorder, administering a therapeutically effective amount of a compound of the invention to the subject, and determining the status of the serotonin-receptor-related disorder after an initial period of treatment, wherein the modulation (e.g., improvement) of the status indicates efficacy of the treatment.

In one aspect, methods of selecting a subject suffering from or susceptible to a serotonin-receptor-related disorder for treatment with a compound of the invention comprise determining the pre-treatment status of the serotonin-receptor-related disorder, administering a therapeutically effective amount of a compound of the invention to the subject, and determining the status (of the serotonin-receptor-related disorder after an initial period of treatment with the compound, wherein the modulation (e.g., improvement) of the status is an indication that the serotonin-receptor-related disorder is likely to have a favorable clinical response to treatment with a compound of the invention.

The subject may be at risk of a serotonin-receptor-related disorder, may be exhibiting symptoms of a serotonin-receptor-related disorder, may be susceptible to a serotonin-receptor-related disorder and/or may have been diagnosed with a serotonin-receptor-related disorder.

The initial period of treatment may be the time in which it takes to establish a stable and/or therapeutically effective blood serum level of the compound, or the time in which it take for the subject to clear a substantial portion of the compound, or any period of time selected by the subject or healthcare professional that is relevant to the treatment.

If the modulation of the status indicates that the subject may have a favorable clinical response to the treatment, the subject may be treated with the compound. For example, the subject can be administered therapeutically effective dose or doses of the compound.

Kits of the invention include kits for treating a serotonin-receptor-related disorder in a subject. The invention also includes kits for assessing the efficacy of a treatment for a serotonin-receptor-related disorder in a subject, monitoring the progress of a subject being treated for a serotonin-receptor-related disorder, selecting a subject with a serotonin-receptor-related disorder for treatment according to the invention, and/or treating a subject suffering from or susceptible to a serotonin-receptor-related disorder. The kit may include a compound of the invention, for example, a compound of any of formula I-IV, pharmaceutically acceptable esters, salts, and prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of an treatment for a serotonin-receptor-related disorder may be packaged with a kit for monitoring the progress of a subject being treated for a serotonin-receptor-related disorder according to the invention.

Certain of the present methods can be performed on cells in culture, e.g. in vitro or ex vivo, or on cells present in an animal subject, e.g., in vivo. Compound of the invention can be initially tested in vitro using cells that express a serotonin receptor (see, e.g., the Examples, infra).

Alternatively, the effects of compound of the invention can be characterized in vivo using animals models.

4. Pharmaceutical Compositions

The invention also provides a pharmaceutical composition, comprising an effective amount of a compound of the invention (e.g., a compound capable of treating or preventing a condition as described herein, e.g., a compound of any formula herein or otherwise described herein) and a pharmaceutically acceptable carrier.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; ($1_3$) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, more preferably from about 10 per cent to about 30 per cent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the present invention is administered at a concentration or amount of about 0.001 mg to about 100 mg per kilogram of body weight, about 0.01-about 50 mg/kg or about 10 mg-about 30 mg/kg of body weight. Ranges intermediate to the above-recited values are also intended to be part of the invention.

The invention is further illustrated by the following examples which are intended to illustrate but not limit the scope of the invention.

EXAMPLES

Chemical Synthesis:

General. All exemplified target compounds are fully analyzed and characterized (mp, TLC, CHN, HPLC-MS, $^1$-NMR, $^{13}$C-NMR) prior to submission for biological evaluation. Melting points are uncorrected. Thin-layer chromatography was carried out on Baker Si 250F plates. Visualization was accomplished with ultraviolet exposure or with phosphomolybdic acid. Flash chromatography was carried out on silica gel (60 mM). Elemental analyses were performed at Atlantic Microlab. HPLC-MS were carried out on a Agilent 1100 series HPLC-Mass Spectrometer. $^1$H and $^{13}$C NMR spectra were recorded at 300 and 75 MHz, respectively on a Jeol Eclipse 300 Spectrometer. NMR assignments are based on a combination of the $^1$H, $^{13}$C, $^1$H COSY, HMBC and HMQC spectra. Anhydrous methylene chloride, tetrahydrofuran, and dimethylformamide are Aldrich Sure/Seal™, and other materials are reagent grade.

Example 1

3-(2-Dimethylaminoethyl)-7-fluoro-1-methyl-1H-indol-4-ol (Compound 11, O-3804)

Step One: 3-(2-Dimethylaminoethyl)-4-benzyloxy-7-fluoro-1-methyl-1H-indole, Compound 22

A solution of compound 1 (prepared according to the procedure of Blair, J., Kurrasch-Orbaugh, D., Marona-Lewicka, D., Cumbay, M., Watts, V., Barker, E., Nichols, D. "Effect of Ring Fluorination of Hallucinogenic Tryptamines" J. Med. Chem. 2000, 43, 4701), (2.77 g, 8.9 mmol, 1 eq,) in 70 mL of anhydrous DMF was cooled in a wet ice bath. Sodium hydride (60 wt % dispersion in oil, 534 mg, 13.3 mmol, 1.5 eq) was added. After stirring at 0° C. for 45 minutes, methyl iodide (9.36 mmol, 1.05 eq), as a 0.3 M solution in anhydrous DMF, was added dropwise. After stirring for 1 hour at room temperature, saturated aqueous NaHCO$_3$ was added, and the product was extracted into ethyl acetate. Purification by flash chromatography provided 2.78 g of 2 as a gold oil. Yield: 95%. $^1$H-NMR (300 MHz, CDCl$_3$), δ=2.13 (s, 6H), 2.54 (m, 2H), 2.96 (m, 2H), 3.89 (s, 3H), 5.12 (s, 2H), 6.31 (dd, 1H), 6.69 (m, 2H), 7.30-7.65 (m, 5H). MS: m/z 327 (M+1).

Step Two: 3-(2-Dimethylaminoethyl)-7-fluoro-1-methyl-1H-indol-4-ol (Compound 11, O-3804).

A solution of 2 (2.78 g, 8.5 mmol) in 40 mL of MeOH was charged with Pd(OH)$_2$ (500 mg) and stirred under 1 atm of H$_2$ for 4 hours. Following removal of the catalyst, crystallization from MeOH provided 1.42 g of 11 (O-3804) as a beige powder. Yield: 69%. Melting point: 134-138° C. $^1$H-NMR (300 MHz, CDCl$_3$), δ=2.36 (s, 6H), 2.66 (m, 2H), 2.89 (m, 2H), 3.88 (s, 3H), 6.35 (dd, 1H), 6.62 (s, 1H), 6.69 (dd, 1H). MS: m/z 237 (M+1). Analysis calculated for C$_{13}$H$_{17}$FN$_2$O: C, 66.08; H, 7.25; N, 11.86. found: C, 66.04; H, 7.26; N, 11.75.

Example 2

3-(2-Dimethylaminoethyl)-7-fluoro-1-ethyl-1H-indol-4-ol (Compound 12, O-3943)

A solution of compound 1 (115 mg, 0.37 mmol, 1 eq) in 3 mL of anhydrous DMF was cooled in a wet ice bath. Sodium hydride (60 wt % dispersion in oil, 23 mg, 0.57 mmol, 1.5 eq) was added. After stirring at 0° C. for 45 minutes, ethyl iodide (0.42 mmol, 1.1 eq), as a 0.3 M solution in anhydrous DMF, was added dropwise. After stirring for 2-3 hours at room temperature, saturated aqueous NaHCO$_3$ was added, and the product was extracted into ethyl acetate. Removal of the solvent provided 3 in quantitative yield, used in the next step without further purification.

Compound 3 was dissolved in 4 mL of MeOH, Pd(OH)$_2$ (25 mg) was added, and the mixture was stirred under 1 atm of H$_2$ for 4 hours. Following removal of the catalyst, purification by flash column chromatography provided 52 mg of 12 (O-3943) as a tan solid. Yield: 56%. Melting point: 114-120° C. $^1$H-NMR (300 MHz, CDCl$_3$), δ=1.42 (t, 3H), 2.36 (s, 6H), 2.68 (m, 2H), 2.90 (m, 2H), 4.21 (q, 2H), 6.36 (dd, 1H), 6.68-6.74 (m, 2H). MS m/z 251 (M+1). Analysis calculated for C$_{14}$H$_{19}$FN$_2$O: C, 67.18; H, 7.65; N, 11.19. found: C, 67.29; H, 7.66; N, 11.04.

Example 3

3-(2-Dimethylaminoethyl)-7-fluoro-1-propyl-1H-indol-4-ol (Compound 13, O-3952)

Following the procedure used to prepare compound 12, compound 1 (124 mg, 0.40 mmol) was treated with n-propyl iodide, followed by debenzylation, and purification by flash chromatography, to give 66 mg of 13 (O-3952) as a tan solid. Yield: 62%. Melting point: 75-79° C. $^1$H-NMR (300 MHz, CDCl3), δ=0.90 (t, 3H), 1.81 (m, 2H), 2.36 (s, 6 H), 2.68 (m, 2H), 2.90 (m, 2H), 4.12 (t, 2H), 6.36 (dd, 1H), 6.67-6.74 (m, 2H). MS: m/z 265 (M+1). Analysis calculated for C$_{15}$H$_{21}$FN$_2$O: C, 68.16; H, 8.01; N, 10.60. found: C, 67.93; H, 7.91; N, 10.35.

Example 4

3-(2-Dimethylaminoethyl)-7-fluoro-1-(2-fluoroethyl)-1H-indol-4-ol (Compound 14, O-3975)

Following the procedure used to prepare compound 11, compound 1 (127 mg, 0.41 mmol) was treated with 2-fluoroethyl bromide followed by debenzylation, and purification by flash chromatography to give 75 mg of 14 (O-3975) as a tan solid. Yield: 68%. Melting point: 97-101° C. $^1$H-NMR (300 MHz, CDCl$_3$), δ=2.36 (s, 6H), 2.68 (m, 2H), 2.90 (m, 2H), 4.42 (t, 1H), 4.50 (t, 1H), 4.64 (t, 1H), 4.79 (t, 1H), 6.38 (dd, 1H), 6.70-6.79 (m, 2H). MS: m/z 269 (M+1). Analysis calculated for $C_{14}H_{18}F_2N_2O$: C, 62.25; H, 6.79; N, 10.37. found: C, 62.11; H, 6.63; N, 10.34.

Example 5

3-(2-Dimethylaminoethyl)-7-fluoro-1-butyl-1H-indol-4-ol (Compound 15, O-4205)

Step One: 3-(2-Dimethylaminoethyl)-4-benzyloxy-7-fluoro-1-butyl-1H-indole (Compound 6)

Following the procedure used for the preparation of compound 2, compound 1 (108 mg, 0.35 mmol) was treated with n-butyl iodide to provide 90 mg of 6 as a yellow oil. Yield: 71%. $^1$H-NMR (300 MHz, CDCl3), δ=0.92 (t, 3H), 1.31 (m, 2H), 1.77 (m, 2H), 2.15 (s, 6H), 2.53 (m, 2H), 2.99 (m, 2H), 4.17 (t, 2H), 5.13 (s, 2H), 6.32 (dd, 1H), 6.65-6.74 (m, 2H), 7.29-7.49 (m, 5H). MS: m/z 369 (M+1).

Step Two: 3-(2-Dimethylamino-ethyl)-7-fluoro-1-butyl-1H-indol-4-ol (Compound 15, O-4205)

A solution of 6 (90 mg, 0.24 mmol) in 5 mL of MeOH was charged with Pd(OH)$_2$ (30 mg) and stirred under 1 atm of H$_2$ for 4 hours. Following removal of the catalyst, purification by flash column chromatography provided 52 mg of 15 (O-4205) as a white solid. Yield: 78%. Melting point: 87-90° C. $^1$H-NMR (300 MHz, CDCl$_3$), δ=0.93 (t, 3H), 1.30 (m, 2H), 1.77 (m, 2H), 2.37 (s, 6H), 2.68 (m, 2H), 2.90 (m, 2H), 4.15 (t, 2H), 6.35 (dd, 1H), 6.65-6.75 (m, 2H). MS: m/z 279 (M+1). Analysis calculated for $C_{16}H_{23}FN_2O$: C, 69.04; H, 8.33; N, 10.06. found: C, 69.03; H, 8.46; N, 9.97.

Example 6

3-(2-Dimethylaminoethyl)-7-fluoro-1-cyclopropylmethyl-1H-indol-4-ol (Compound 16, O-4322)

Step One: 3-(2-Dimethylaminoethyl)-4-benzyloxy-7-fluoro-1-cyclopropylmethyl-1H-indole (Compound 7)

Following the procedure used to prepare compound 2, compound 1 (148 mg, 0.48 mmol) and cyclopropylmethyl bromide (1.0 mmol) gave compound 7 (112 mg) as a yellow oil. Yield: 64%. $^1$H NMR (300 MHz, CDCl$_3$): 7.46-7.50 (m, 2H), 7.32-7.40 (m, 3H), 6.83 (s, 1H), 6.68 (dd, J=12.4, 8.7, 1H), 6.32 (dd, J=8.4, 2.7, 1H), 5.13 (s, 2H), 4.06 (d, J=6.9, 2H), 2.92-2.98 (m, 2H), 2.54-2.60 (m, 2H), 2.12 (s, 6H), 1.23-1.26 (m, 1 H), 0.52-0.58 (m, 2H), 0.33-0.36 (m, 2H). Mass spectrum: m/z 367 (M+1).

Step Two: 3-(2-Dimethylaminoethyl)-7-fluoro-1-cyclopropylmethyl-1H-indol-4-ol (Compound 16, O-4322)

Following the procedure used to prepare compound 15, compound 7 (101 mg, 0.28 mmol) gave 66 mg of compound 16 as a beige foam. Yield: 86%. $^1$H NMR (300 MHz, CDCl$_3$): 6.80 (s, 1H), 6.71 (dd, J=12.6, 8.4, 1H), 6.35 (dd, J=8.4, 3.3, 1H), 4.04 (d, J=6.6, 2H), 2.89-2.93 (m, 2H), 2.66-2.70 (m, 2H), 2.35 (s, 6H), 1.22-1.24 (m, 1 H), 0.54-0.58 (m, 2H), 0.31-0.34 (m, 2H). Mass spectrum: m/z 277 (M+1). Analysis calculated for $C_{16}H_{21}FN_2O$ 0.1 $H_2O$: C, 69.09; H, 7.68; N, 10.07. found: C, 68.98; H, 7.67; N, 9.85.

Example 7

3-(2-Dimethylaminoethyl)-7-fluoro-1-iso-propyl-1H-indol-4-ol (Compound 17, O-4324)

Step One: 3-(2-Dimethylaminoethyl)-4-benzyloxy-7-fluoro-1-isopropyl-1H-indole (Compound 8)

Following the procedure used to prepare compound 2, compound 1 (148 mg, 0.47 mmol), sodium hydride (1.50 mmol) and isopropyl iodide (1.5 mmol) gave compound 8 (130 mg) as a yellow oil. Yield: 78%. $^1$H NMR (300 MHz, CDCl$_3$): 7.37-7.44 (m, 2H), 7.30-7.36 (m, 3H), 6.91 (s, 1H), 6.68 (dd, J=12.4, 8.4, 1H), 6.32 (dd, J=8.4, 2.7, 1H), 5.13 (s, 2H). 4.90-5.13 (m, 1H), 2.92-2.98 (m, 2H), 2.54-2.60 (m, 2H), 2.12 (s, 6H), 1.48 (d, J=6.9, 6H). Mass spectrum: m/z 355 (M+1).

Step Two: 3-(2-Dimethylaminoethyl)-7-fluoro-1-isopropyl-1H-indol-4-ol (Compound 17, O-4324)

Following the procedure used to prepare compound 15, compound 8 (110 mg, 0.31 mmol) gave compound 17 (66 mg) as a beige solid. Yield: 80%. Melting point: 108-110° C. $^1$H NMR (300 MHz, CDCl$_3$): 6.86 (s, 1H), 6.71 (dd, J=12.9, 8.4, 1H), 6.36 (dd, J=8.1, 3.0, 1H), 4.92-5.01 (m, 1H), 2.88-2.94 (m, 2H), 2.65-2.70 (m, 2H), 2.36 (s, 6H), 1.46 (d, J=6.6, 6H). Mass spectrum: m/z 265 (M+1). Analysis calculated for $C_{15}H_{21}FN_2O$: C, 68.16; H, 8.01; N, 10.60. found: C, 67.98; H, 8.02; N, 10.45.

Example 8

3-(2-Dimethylaminoethyl)-7-fluoro-1-methylsulfonyl-1H-indol-4-ol (Compound 18, O-4323)

Step One: 3-(2-Dimethylaminoethyl)-4-benzyloxy-7-fluoro-1-methylsulfonyl-1H-indole (Compound 9)

To a solution of compound 1 (160 mg, 0.51 mmol) in DMF (5 ml) was added sodium hydride (1.5 mmol) at 0° C. After stirring for 5 minutes, methanesulfonyl chloride (2.0 mmol) was added dropwise over 5 minutes. The reaction mixture was stirred at 0-5° C. for 15 minutes, then gradually heated to 110° C. and stirred at 110° C. for 12 hours, cooled to 25° C., quenched by addition of water (20 ml), and extracted with EtOAc (45×2 ml). The extracts were collected, washed with brine, and dried over MgSO$_4$. Removal of the solvent followed by column chromatography provided compound 9 (72 mg) as an oil. Yield: 36%. $^1$H NMR (300 MHz, CDCl$_3$):

7.32-7.48 (m, 5H), 6.99 (dd, J=11.7, 8.4, 1H), 6.62 (dd, J=12, 3.6, 1H), 5.15 (s, 2H), 3.43 (s, 3H), 2.92-2.98 (m, 2H), 2.54-2.60 (m, 2H), 2.14 (s, 6H). Mass spectrum: m/z 391 (M+1).

Step Two: 3-(2-Dimethylaminoethyl)-7-fluoro-1-methylsulfonyl-1H-indol-4-ol (Compound 18, O-4323)

Following the procedure used to prepare compound 15, compound 9 (70 mg, 0.18 mmol), gave compound 18 (24 mg) as a beige solid. Yield: 45%. Melting point 181-183° C. $^1$H NMR (300 MHz, CDCl$_3$): 7.22 (s, 1H), 6.90 (dd, J=11.4, 8.4, 1H), 6.62 (dd, J=8.4, 3.3, 1H), 3.44 (s, 2H), 2.86-2.91 (m, 2H), 2.70-2.76 (m, 2H), 2.38 (s, 6H). Mass spectrum: m/z 301 (M+1). Analysis calculated for $C_{13}H_{17}FN_2O_3S$ 0.1 $CH_2Cl_2$: C, 50.95; H, 5.61; N, 9.07. found: C, 51.07; H, 5.59; N, 8.98.

Example 9

3-(2-Dimethylaminoethyl)-7-fluoro-1-ethylsulfonyl-1H-indol-4-ol (Compound 19, O-4321)

Step One: 3-(2-Dimethylaminoethyl)-4-benzyloxy-7-fluoro-1-ethylsulfonyl-1H-indole, 10

Following the procedure used to prepare compound 9, compound 1 (150 mg, 0.48 mmol), sodium hydride (1.5 mmol) and ethanesulfonyl chloride (1.92 mmol), gave compound 10 (98 mg) as an oil. Yield: 50%. $^1$H NMR (300 MHz, CDCl$_3$): 7.32-7.48 (m, 5H), 6.92 (dd, J=11.7, 8.7, 1H), 6.62 (dd, J=9.3, 3.0, 1H), 5.14 (s, 2H), 3.58 (q, J=7.5, 2H), 2.94-3.04 (m, 2H), 2.54-2.60 (m, 2H), 2.14 (s, 6H), 1.34 (t, J=7.5, 3H). Mass spectrum: m/z 405 (M+1).

Step Two: 3-(2-Dimethylaminoethyl)-7-fluoro-1-ethylsulfonyl-1H-indol-4-ol (Compound 19, (O-4321)

Following the procedure used to prepare compound 15, compound 10 (95 mg, 0.23 mmol) gave compound 19 (41 mg) as a beige foam. Yield: 57%. $^1$H NMR (300 MHz, CDCl$_3$): 7.21 (s, 1H), 6.92 (dd, J=11.7, 8.4, 1H), 6.62 (dd, J=9.0, 3.6, 1H), 3.62 (q, J=7.5, 2H), 2.88-2.93 (m, 2H), 2.72-2.76 (m, 2H), 2.38 (s, 6H), 1.32 (t, J=7.5, 3 H). Mass spectrum: m/z 315 (M+1). Analysis calculated for $C_{14}H_{19}FN_2O_3S$ 0.1 $H_2O$: C, 53.18; H, 6.12; N, 8.86. found: C, 52.98; H, 6.31; N, 8.63.

Example 10

3-(2-Dimethylaminoethyl)-7-fluoro-1-(2-propen-1-yl)-1H-indol-4-ol (Compound 20, O-4270)

A solution of compound 1 (497 mg, 1.59 mmol) in 40 mL of MeOH was charged with Pd(OH)$_2$ (110 mg) and stirred under 1 atm of H$_2$ for 4 hours. Following removal of the catalyst and evaporation of the solvent, the crude product was dissolved in 15 mL of anhydrous THF. After cooling to −78° C., n-butyllithium (3.30 mmol, 2.1 eq) was added dropwise. After stirring at −78° C. for 20 minutes, allyl bromide (0.3 mmol, 1 eq), as a 0.3 M solution in THF, was added dropwise. After warming to room temperature, the reaction was stirred for 2 hours and then quenched by addition of H$_2$O. Extraction into diethyl ether, followed by multiple chromatographies, provided 6 mg of 20 as a white solid. Yield: 1.5%. $^1$H-NMR (300 MHz, CDCl$_3$), δ=2.36 (s, 6H), 2.67 (m, 2H), 2.90 (m, 2H), 4.79 (m, 2H), 5.03 (d, 1H), 5.14 (m, 1H), 6.02 (m, 1H), 6.36 (dd, 1H), 6.70 (m, 2H). MS: m/z 263 (M+1).

Example 11

3-(2-Dimethylaminoethyl)-7-fluoro-1-methyl-1H-indol-4-phosphate (Compound 21, O-3944)

Compound 11 (750 mg, 3.18 mmol, 1 eq) was dissolved in 70 mL anhydrous THF. Anhydrous diisopropylamine (107 mg, 1.6 mmol, 0.33 eq) was added and the mixture cooled to −78° C. N-Butyllithium (4 mmol, 1.25 eq) was added rapidly and the mixture stirred at −78° C. for 5-7 minutes. Tetrabenzyl pyrophosphate (prepared according to the procedure of Khorana, H. and Todd, A., J. Chem. Soc., 2257-2260, 1953) (2.15 g, 4 mmol, 1.25 eq) was added rapidly and the reaction mixture then transferred to a −20° C. ice/salt bath. After stirring for 2 hours, saturated aqueous ammonium chloride was added. The crude intermediate was isolated by extraction followed by standard workup, then dissolved in 70 mL of MeOH, charged with Pd(OH)$_2$ (420 mg) and stirred under 1 atm of H$_2$. Following removal of the catalyst, the pH was adjusted to approximately 5 using ion exchange resin. Removal of the solvent followed by crystallization from H$_2$O provided 530 mg of 21 as a white solid. Yield: 52%. Melting point: 184-186° C. $^1$H-NMR (300 MHz, D$_2$O), δ=2.72 (s, 6H), 3.09 (m, 2H), 3.27 (m, 2H), 3.72 (d, 3H), 6.70 (m, 2H), 6.88 (s, 1H). MS: m/z 237 (M+1-H2PO3). Analysis calculated for $C_{13}H_{18}FN_2O_4P$ 0.25 $H_2O$: C, 48.68; H, 5.81; N, 8.73; F, 5.92. found: C, 48.65; H, 5.70; N, 8.68; F, 5.80.

Example 12

3-(2-Dimethylaminoethyl)-7-fluoro-1-propyl-1H-indol-4-phosphate (Compound 22, O-4309)

Following the procedure used to prepare compound 21, compound 13 (579 mg, 2.19 mmol) provided 418 mg of 22 as a white solid. Yield: 55%. Melting point: 209-211° C. $^1$H-NMR (300 MHz, D$_2$O): δ=0.70 (t, 3H), 1.68 (m, 2H), 2.80 (s, 6H), 3.17 (m, 2H), 3.33 (m, 2H), 4.09 (t, 2H), 6.75-6.78 (m, 2H), 7.05 (s, 1H). MS: m/z 345 (M+1). Analysis calculated for $C_{15}H_{22}FN_2O_4P$ 0.6 $H_2O$: C, 50.73; H, 6.58; N, 7.89. found: C, 50.69; H, 6.62; N, 7.90.

Example 13

3-(2-Dimethylaminoethyl)-6-fluoro-1-methyl-1H-indol-4-ol (Compound 32, O-4244)

Step One: 3-(2-Dimethylaminoethyl)-4-benzyloxy-6-fluoro-1-methyl-1H-indole (Compound 24)

Following the procedure used to prepare compound 2, compound 23 (prepared according to the procedure of Blair, J., Kurrasch-Orbaugh, D., Marona-Lewicka, D., Cumbay, M., Watts, V., Barker, E., Nichols, D. "Effect of Ring Fluorination of Hallucinogenic Tryptamines" *J. Med. Chem.* 2000, 43, 4701), (624 mg, 2 mmol), sodium hydride (6 mmol) and methyl iodide (2.4 mmol) gave compound 24 (520 mg) as a white solid. Yield: 80%. Melting point: 156-158° C. $^1$H NMR (300 MHz, CDCl$_3$): 7.47-7.50 (m, 2H), 7.32-7.40 (m, 3H), 6.71 (s, 1H), 6.56 (dd, J=9.3, 1.9, 1H), 6.34 (dd, J=11.7, 1.9, 1H), 5.18 (s, 2H), 3.69 (s, 3H), 2.92-2.98 (m, 2H), 2.54-2.60 (m, 2H), 2.13 (s, 6H). Mass spectrum: m/z 327 (M+1).

Step Two: 3-(2-Dimethylaminoethyl)-6-fluoro-1-methyl-1H-indol-4-ol (Compound 32, O-4244)

Following the procedure used to prepare compound 15, compound 24 (500 mg, 1.53 mmol) gave compound 32 (298 mg) as a beige solid. Yield: 83%. Melting point: 132-134° C. $^1$H NMR (300 MHz, CDCl$_3$): 6.60 (s, 1H), 6.44 (dd, J=9.6, 2.1, 1H), 6.31 (dd, J=11.4, 2.1, 1H), 3.66 (s, 3H), 2.82-2.90 (m, 2H), 2.64-2.70 (m, 2H), 2.38 (s, 6H). Mass spectrum: m/z 237 (M+1), 192 [(M+1)-HNMe$_2$]. Analysis calculated for C$_{13}$H$_{17}$FN$_2$O: C, 66.08; H, 7.25; N, 11.86. found: C, 66.03; H, 7.35; N, 11.75.

Example 14

3-(2-Dimethylaminoethyl)-6-fluoro-1-ethyl-1H-indol-4-ol (Compound 33, O-4284)

Step One: 3-(2-Dimethylaminoethyl)-4-benzyloxy-6-fluoro-1-ethyl-1H-indole (Compound 25)

Following the procedure used to prepare compound 2, compound 23 (156 mg, 0.5 mmol), sodium hydride (1.50 mmol) and ethyl iodide (0.75 mmol) gave compound 25 (130 mg) as a white solid. Yield: 76%. Melting point: 172-174° C. $^1$H NMR (300 MHz, CDCl$_3$): 7.46-7.50 (m, 2H), 7.32-7.40 (m, 3H), 6.70 (s, 1H), 6.56 (dd, J=9.3, 1.9, 1H), 6.32 (dd, J=11.7, 1.9, 1H), 5.18 (s, 2H), 3.98 (q, J=7.2, 2H), 2.92-2.98 (m, 2H), 2.54-2.60 (m, 2H), 2.13 (s, 6H). Mass spectrum: m/z 341 (M+1).

Step Two: 3-(2-Dimethylaminoethyl)-6-fluoro-1-ethyl-1H-indol-4-ol (Compound 33, O-4284)

Following the procedure used to prepare compound 15, compound 25 (98 mg, 0.29 mmol) gave compound 33 (60 mg) as a beige foam. Yield: 82%. $^1$H NMR (300 MHz, CDCl$_3$): 6.70 (s, 1H), 6.45 (dd, J=9.6, 2.1, 1H), 6.32 (dd, J=11.4, 2.1, 1H), 3.98 (q, J=7.2, 2H), 2.82-2.90 (m, 2H), 2.64-2.70 (m, 2H), 2.40 (s, 6H), 1.40 (t, J=7.2, 3H). Mass spectrum: m/z 251 (M+1). Analysis calculated for C$_{14}$H$_{19}$FN$_2$O: C, 67.18; H, 7.65; N, 11.20. found: C, 67.09; H, 7.79; N, 10.94.

Example 15

3-(2-Dimethylaminoethyl)-6-fluoro-1-propyl-1H-indol-4-ol (Compound 34, O-4285)

Step One: 3-(2-Dimethylaminoethyl)-4-benzyloxy-6-fluoro-1-propyl-1H-indole (Compound 26)

Following the procedure used to prepare compound 2, compound 23 (156 mg, 0.5 mmol), sodium hydride (1.50 mmol) and n-propyl iodide (0.75 mmol) gave compound 26 (106 mg) as a white solid. Yield: 60%. Melting point: 144-146° C. $^1$H NMR (300 MHz, CDCl$_3$): 7.46-7.49 (m, 5H), 6.95 (s, 1H), 6.64 (dd, J=9.3, 1.9, 1H), 6.46 (dd, J=11.7, 1.9, 1H), 5.08 (s, 2H), 3.92 (t, J=7.2, 2H), 3.52-3.57 (m, 2H), 3.12-3.20 (m, 2H), 3.0 (s, 6H), 1.79 (m, 2H), 0.92 (t, J=7.2, 3H). Mass spectrum: m/z 355 (M+1).

Step Two: 3-(2-Dimethylaminoethyl)-6-fluoro-1-propyl-1H-indol-4-ol (Compound 34, O-4285)

Following the procedure used for the preparation of compound 15, compound 26 (106 mg, 0.30 mmol) gave compound 34 (62 mg) as a beige solid. Yield: 78%. Melting point 104-106° C. $^1$H NMR (300 MHz, CDCl$_3$): 6.68 (s, 1H), 6.46 (dd, J=9.6, 2.1, 1H), 6.30 (dd, J=11.4, 2.1, 1H), 3.87 (t, J=7.2, 2H), 2.82-2.90 (m, 2H), 2.64-2.70 (m, 2H), 2.38 (s, 6H), 1.78 (m, 2H), 0.92 (t, J=7.5, 3H). Mass spectrum: m/z 265 (M+1). Analysis calculated for C$_{15}$H$_{21}$FN$_2$O: C, 68.16; H, 8.01; N, 10.60. found: C, 67.99; H, 8.02; N, 10.43.

Example 16

3-(2-Dimethylaminoethyl)-6-fluoro-1-butyl-1H-indol-4-ol (Compound 35, O-4286)

Step One: 3-(2-Dimethylaminoethyl)-4-benzyloxy-6-fluoro-1-butyl-1H-indole, 27

Following the procedure used to prepare compound 2, compound 23 (0.5 mmol), sodium hydride (1.50 mmol) and butyl iodide (0.75 mmol) gave compound 27 (112 mg). Yield: 61%. Melting point 86-89° C. $^1$H NMR (300 MHz, CDCl$_3$): 7.46-7.50 (m, 2H), 7.34-7.41 (m, 3H), 6.73 (s, 1H), 6.56 (dd, J=9.3, 1.9, 1H), 6.33 (dd, J=11.7, 1.9, 1H), 5.17 (s, 2H), 3.92 (q, J=7.2, 2H), 2.92-2.98 (m, 2H), 2.54-2.60 (m, 2H), 2.14 (s, 6H), 1.72-1.78 (m, 2H), 0.93 (t, J=7.2, 3H). Mass spectrum: m/z 369 (M+1).

Step Two: 3-(2-Dimethylaminoethyl)-6-fluoro-1-butyl-1H-indol-4-ol (Compound 35, O-4286)

Following the same procedure used for the preparation of compound 15, compound 27 (100 mg, 0.27 mmol) gave compound 35 (60 mg) as a beige solid. Yield: 80%. Melting point 92-95° C. $^1$H NMR (300 MHz, CDCl$_3$): 6.68 (s, 1H), 6.46 (dd, J=9.3, 2.1, 1 H), 6.30 (dd, J=11.7, 2.1, 1H), 3.89 (t, J=7.2, 2H), 2.82-2.90 (m, 2H), 2.64-2.68 (m, 2H), 2.38 (s, 6H), 1.70-1.78 (m, 2H), 1.28-1.34 (m, 2H), 0.92 (t, J=7.2, 3H). Mass spectrum: m/z 279 (M+1). Analysis calculated for C$_{16}$H$_{23}$FN$_2$O: C, 69.04; H, 8.33; N: 10.06. found: C, 68.81; H, 8.44; N, 9.89.

Example 17

3-(2-Dimethylaminoethyl)-6-fluoro-1-cyclopropylmethyl-1H-indol-4-ol (Compound 36, O-4287)

Step One: 3-(2-Dimethylaminoethyl)-4-benzyloxy-6-fluoro-1-cyclopropylmethyl-1H-indole (Compound 28)

Following the procedure used to prepare compound 2, compound 23 (0.5 mmol), sodium hydride (1.50 mmol) and cyclopropylmethyl bromide (0.75 mmol) gave compound 28 (129 mg). Yield: 70%. Melting point: 121-123° C. $^1$H NMR (300 MHz, CDCl$_3$): 7.46-7.50 (m, 2H), 7.32-7.40 (m, 3H), 6.85 (s, 1H), 6.62 (dd, J=9.6, 1.9, 1H), 6.34 (dd, J=11.7, 1.9, 1H), 5.18 (s, 2H), 3.80 (d, J=6.9, 2H), 2.92-2.98 (m, 2H), 2.54-2.60 (m, 2H), 2.12 (s, 6H), 2.17-2.20 (m, 2H), 0.56-0.61 (m, 2H), 0.30-0.34 (m, 2H). Mass spectrum: m/z 367 (M+1).

Step Two: 3-(2-Dimethylaminoethyl)-6-fluoro-1-cyclopropylmethyl-1H-indol-4-ol (Compound 36, O-4287)

Following the procedure used for the preparation of compound 15, compound 28 (105 mg, 0.28 mmol) gave compound 36 (60 mg) as a beige solid. Yield: 76%. Melting point: 110-112° C. $^1$H NMR (300 MHz, CDCl$_3$): 6.80 (s, 1H), 6.48

(dd, J=9.6, 2.1, 1H), 6.31 (dd, J=11.7, 2.1, 1H), 3.77 (d, J=6.9, 2H), 2.82-2.90 (m, 2H), 2.64-2.70 (m, 2H), 2.36 (s, 6H), 1.22-1.24 (m, 1H), 0.58-0.62 (m, 2H), 0.31-0.34 (m, 2H). Mass spectrum: m/z 277 (M+1). Analysis calculated for $C_{16}H_{21}FN_2O$: C, 69.54; H, 7.66; N, 10.14. found: C, 69.48; H, 7.78; N, 9.93.

Example 18

3-(2-Dimethylaminoethyl)-6-fluoro-1-isopropyl-1H-indol-4-ol (Compound 37, O-4310)

Step One: 3-(2-Dimethylaminoethyl)-4-benzyloxy-6-fluoro-1-isopropyl-1H-indole (Compound 29)

Following the procedure used to prepare compound 2, compound 23 (0.5 mmol), sodium hydride (1.50 mmol) and isopropyl iodide (0.75 mmol) gave compound 29 (128 mg) as a yellow oil. Yield: 72%. $^1$H NMR (300 MHz, $CDCl_3$): 7.46-7.50 (m, 2H), 7.32-7.40 (m, 3H), 6.85 (s, 1H), 6.62 (dd, J=9.9, 1.9, 1H), 6.34 (dd, J=11.7, 1.9, 1H), 5.14 (s, 2H), 4.40-4.47 (m, 1H), 2.92-2.98 (m, 2H), 2.54-2.60 (m, 2H), 2.12 (s, 6H), 1.46 (d, J=6.6, 6H). Mass spectrum: m/z 355 (M+1).

Step Two: 3-(2-Dimethylaminoethyl)-6-fluoro-1-isopropyl-1H-indol-4-ol (Compound 37, O-4310)

Following the procedure used to prepare compound 15, compound 29 (120 mg, 0.33 mmol) gave compound 37 (78 mg) as a beige foam. Yield: 86%. $^1$H NMR (300 MHz, $CDCl_3$): 6.79 (s, 1H), 6.52 (dd, J=9.3, 2.1, 1H), 6.30 (dd, J=11.7, 2.1, 1H), 4.38-4.44 (m, 1H), 2.88-2.94 (m, 2H), 2.67-2.71 (m, 2H), 2.38 (s, 6H), 1.43 (d, J=6.6, 6 H). Mass spectrum: m/z 265 (M+1). Analysis calculated for $C_{15}H_{21}FN_2O$: C, 68.16; H, 8.01; N, 10.60. found: C, 68.10; H, 8.11; N, 10.40.

Example 19

3-(2-Dimethylaminoethyl)-6-fluoro-1-methylsulfonyl-1H-indol-4-ol (Compound 38, O-4320)

Step One: 3-(2-Dimethylaminoethyl)-4-benzyloxy-6-fluoro-1-methylsulfonyl-1H-indole (Compound 30)

Following the procedure used to prepare compound 9, compound 23 (120 mg, 0.38 mmol), sodium hydride (0.8 mmol) and methanesulfonyl chloride (1.52 mmol) gave compound 30 (91 mg) as a foam. Yield: 61%. $^1$H NMR (300 MHz, $CDCl_3$): 7.34-7.48 (m, 5H), 7.23 (dd, J=11.4, 2.1, 1H), 6.56 (dd, J=11.4, 2.1, 1H), 5.15 (s, 2H), 3.11 (s, 2H), 3.11 (s, 3H), 2.92-2.98 (m, 2H), 2.54-2.60 (m, 2H), 2.14 (s, 6H). Mass spectrum: m/z 391 (M+1).

Step Two: 3-(2-Dimethylaminoethyl)-6-fluoro-1-methylsulfonyl-1H-indol-4-ol (Compound 38, O-4320)

Following the procedure used to prepare compound 15, compound 30 (70 mg, 0.18 mmol) gave compound 38 (24 mg) as a beige solid. Yield: 45%. Melting point 184-186° C. $^1$H NMR (300 MHz, $CDCl_3$): 7.12 (dd, J=9.3, 2.1, 1H), 7.05 (s, 1H), 6.50 (dd, J=11.4, 2.1, 1H), 3.06 (s, 3H), 2.88-2.93 (m, 2H), 2.72-2.78 (m, 2H), 2.38 (s, 6H). Mass spectrum: m/z 301 (M+1). Analysis calculated for $C_{13}H_{17}FN_2O_3S$ 0.05 $CH_2Cl_2$: C, 51.47, H, 5.62; N, 9.20. found: C, 51.66; H, 5.79; N, 8.84.

Example 20

3-(2-Dimethylaminoethyl)-6-fluoro-1-ethylsulfonyl-1H-indol-4-ol (Compound 39, O-4312)

Step One: 3-(2-Dimethylaminoethyl)-4-benzyloxy-6-fluoro-1-ethylsulfonyl-1H-indole (Compound 31)

Following the procedure used to prepare compound 9, compound 23 (130 mg, 0.42 mmol), sodium hydride (1.26 mmol) and ethanesulfonyl chloride (1.68 mmol) gave compound 31 (128 mg) as an oil. Yield: 77%. $^1$H NMR (300 MHz, $CDCl_3$): 7.32-7.48 (m, 5H), 7.22 (dd, J=9.3, 2.1, 1H), 6.54 (dd, J=11.4, 2.1, 1H), 5.14 (s, 2H), 3.24 (q, J=7.5, 2H), 2.92-2.98 (m, 2H), 2.54-2.60 (m, 2H), 2.14 (s, 6H), 1.21 (t, J=7.5, 3H). Mass spectrum: m/z 405 (M+1).

Step Two: 3-(2-Dimethylaminoethyl)-6-fluoro-1-ethylsulfonyl-1H-indol-4-ol (Compound 39, O-4312)

Following the procedure used to prepare compound 15, compound 31 (110 mg, 0.27 mmol) gave compound 39 (56 mg) as a beige foam. Yield: 65%. $^1$H NMR (300 MHz, $CDCl_3$): 7.08 (dd, J=9.6, 2.1, 1H), 7.05 (s, 1H), 6.50 (dd, J=11.4, 2.1, 1H), 3.26 (q, J=7.2, 2H), 2.86-2.90 (m, 2H), 2.72-2.78 (m, 2H), 2.40 (s, 6H), 1.22 (t, J=7.5, 3H). Mass spectrum: m/z 315 (M+1). Analysis calculated for $C_{14}H_{19}FN_2O_3S$: C, 53.49; H, 6.09; N: 8.91. found: C, 53.31; H, 6.30; N, 8.71.

Example 21

Receptor Binding:

For initial screens, a 10 micromolar concentration of each compound (dissolved in 10% DMSO) was incubated with the appropriate receptor preparation and percent inhibition determined for duplicate determinations each performed in duplicate. Where >50% inhibition of specific binding was measured, $K_i$ determinations were then measured by competition binding assays in which concentrations from 1 to 100,000 nM were incubated in duplicate. For each $K_i$ value the data represent the mean+/−SD of computer-derived estimates for N=4 separate determinations, as described (Rothman, R., Baumann, M., Savage, J., Rauser, L., McBride, A., Hufeisen, S., Roth, B. L. "Evidence for Possible Involvement of 5-$HT_{2B}$ Receptors in the Cardiac Valvulopathy Associated with Fenfluramine and other Serotonergic Medications" *Circulation* 2000, 102, 2836; Roth, B. L., Shoham, M., Choudhary, M., Khan, N. "Identification of Conserved Aromatic Residues Essential for Agonist Binding and Second Messenger Production at 5-Hydroxytryptamine 2A Receptors" *Mol. Pharmacol.* 1997, 52, 259; Roth, B. L., Choudhary, M., Khan, N., Uluer, A. "High-affinity Agonist Binding is not Sufficient for Agonist Efficacy at 5-Hydroxytryptamine 2A Receptors: Evidence in Favor of a Modified Ternary Complex Model" *J. Pharmacol. Exp. Ther.* 1997, 280, 576). The results are shown in Table 1.

Receptor binding ($K_i$) in nM. When the standard deviation is given N≧3.

TABLE 1

| Compound | 5-$HT_{2A}$ | 5-$HT_{2B}$ | 5-$HT_{2C}$ |
|---|---|---|---|
| O-3804 | 68.18 | 3.642 | 25.43 |
| O-3943 | 97 ± 35 | 2.5 ± 0.84 | 9.1 ± 3.99 |
| O-3952 | 492 ± 79.3 | 2.795 ± 0.31 | 10.52 ± 2.39 |
| O-3975 | 308.2 ± 61.39 | 2.766 ± 0.31 | 7.736 ± 0.65 |

Example 22

Functional Activity Assays:

Phosphoinositide hydrolysis assays were performed with stably (5-HT$_{2A}$, 5-HT$_{2C}$) or transiently (5-HT$_{2B}$) expressed receptors plated in 24-well culture plates. Transfected cells were loaded with (15 Ci/mmol; 1 mCi/mL) overnight in inositol-free DMEM without serum. The next day, phosphate accumulation assays were performed in a modified Krebs-bicarbonate buffer. K$_{act}$ (nmol/L) and percent V$_{max}$ (relative to 5-HT) values were calculated (Roth, B. L., Shoham, M., Choudhary, M., Khan, N. "Identification of Conserved Aromatic Residues Essential for Agonist Binding and Second Messenger Production at 5-Hydroxytryptamine 2A Receptors" *Mol. Pharmacol.* 1997, 52, 259; Roth, B. L., Choudhary, M., Khan, N., Uluer, A. "High-affinity Agonist Binding is not Sufficient for Agonist Efficacy at 5-Hydroxytryptamine 2A Receptors: Evidence in Favor of a Modified Ternary Complex Model" *J. Pharmacol. Exp. Ther.* 1997, 280, 576). The results are shown in Table 2.

Functional Assay (EC$_{50}$) in nM. Data represent mean EC$_{50}$ values for activation of phospho-inositide hydrolysis in cells expressing human 5-HT$_{2A}$, 5-HT$_{2B}$ or 5-HT$_{2C-INI}$ receptors, relative to serotonin at 100%. When the standard deviation is given, N≧3.

TABLE 2

| Compound | 5-HT$_{2A}$ | 5-HT$_{2B}$ | 5-HT$_{2C}$ |
| --- | --- | --- | --- |
| O-3804 | 129.2 ± 1.438 (125.4% ± 6.225%) | 35.45 ± 1.31 (7.0 ± 0.92%) | 0.5168 ± 1.775 (89.89% ± 5.164%) |
| O-3943 | 12.9 +/− 1.59 | >10,000 | 5.4 ± 2.5 (100%) |
| O-3952 | 1281 +/− 681 (103% +/− 7) | >10,000 | 11 ± 4 (89%) |
| O-3975 | 614 +/− 23 | >10,000 | >2000 |
| O-4205 | Inactive | Inactive | inactive |
| O-4244 | 0.55 +/− 0.2 (61%) | Inactive | 0.66 +/− 0.3 (75%) |
| O-4284 | 2.9 +/− 0.5 (73%) | Inactive | 0.54 +/− 0.2 (73%) |
| O-4285 | 166 +/− 30 (63%) | Inactive | 131 +/− 32 (~75%) |
| O-4286 | Inactive | Inactive | inactive |
| O-4287 | 3744 +/− 1000 (63%) | Inactive | 1158 +/− 450 (41%) |
| O-4310 | 5 +/− 2 (89%) | Inactive | 592 +/− 30 (~50%) |
| O-4312 | inactive | Inactive | inactive |

Example 23

Appetite Suppression Studies in Mice
Acute Assays

Mice were deprived of food, but not water, for 18 hours. They were then injected i.p. with test compounds dissolved in 0.9% NaCl containing 1 mg per ml ascorbic acid for protection against oxidation. Each mouse was placed in an individual cage for 30 minutes and then presented with a small petri dish containing a gel made from gelatin, powdered milk and sucrose. The dish was weighed at zero time and at 15-minute intervals for the next hour in order to quantitate food consumption. Controls were injected with saline-ascorbic acid; ±fenfluramine was used as an active control. Control consumption generally ranged from 1.5 to 2.0 grams. The results are shown in Table 3.

TABLE 3

| Substance | Dosage (mg/kg) | N | Mean food consumption 60 min. after injection: g (±SEM) Saline Control | Mean food consumption 60 min. after injection: g (±SEM) Compound | % of Control | Mean food consumption 90 min. after injection: g (±SEM) Saline Control | Mean food consumption 90 min. after injection: g (±SEM) Compound | % of Control |
| --- | --- | --- | --- | --- | --- | --- | --- | --- |
| +/−Fenfluramine | 3 | 10 | 1.26 (.18) | 1.2 (.12) | 95 | 1.68 (.15) | 1.60 (.14) | 95 |
| | 5 | 9 | 1.47 (.15) | 0.90 (.04)* | 61 | 1.76 (.17) | 1.18 (.17)* | 67 |
| | 10 | 10 | 1.33 (.09) | 0.41 (.11)* | 30 | 1.56 (.1) | 0.56 (.13)* | 35 |
| O-3804 | 10 | 5 | 1.14 (.16) | 1.3 (.14) | 114 | 1.84 (.06) | 1.76 (.15) | 96 |
| | 20 | 10 | 1.49 (.22) | 1.48 (.19) | 99 | 1.74 (.14) | 1.86 (.20) | 107 |
| | 30 | 10 | 1.40 (.11) | 0.79 (.09)* | 56 | 1.79 (.14) | 1.37 (.11) | 77 |
| O-3944 | 10 | 5 | 1.14 (.16) | 0.84 (.17) | 74 | 1.84 (.06) | 1.38 (.13) | 75 |
| | 20 | 15 | 1.45 (.17) | 0.56 (.10)* | 41 | 1.70 (.11) | 1.05 (.14)* | 62 |
| | 30 | 15 | 0.84 (.09) | 0.13 (.05)* | 15 | 1.18 (.11) | 0.65 (.11)* | 55 |
| O-4309 | 10 | 5 | 0.68 (.1) | 0.28 (.06)* | 41 | 1.06 (.09) | 0.68 (0.1)* | 64 |
| | 20 | 10 | 0.74 (.07) | .07 (.02)* | 9 | 1.25 (.08) | 0.22 (.05)* | 18 | pValue <0.05 for compound versus saline control

Example 24

Chronic Assays

Mice were injected i.p. at intervals of 2 or 3 days and weighed repeatedly (6 or 7 total injections). Controls were injected with saline. Weighing and injection were carried out between 11 AM and 1 PM. The results are shown in Table 4.

housed 5 per cage, given free access to standard mouse food and water except during experiments, and maintained in a temperature-controlled room (70° F.). Serotonin and all test drugs were made up with ascorbic acid to protect against oxidation. Two mice, one a control, the other experimental, were tested each time. Each mouse was separately placed into a plexiglas box.

TABLE 4

| | | | | Day 7 | | Day 14 | |
| --- | --- | --- | --- | --- | --- | --- | --- |
| Name of Compound | Dose (mg/kg) | N | Average Starting Weight: g (SEM) | Difference within same group (g) | % Δ from starting weight | Difference within same group (g) | % Δ from starting weight |
| Saline | | 10 | 5 | 43.2 (2.15) | 1.24 | 4.26 | 1.46 | 3.38 |
| ±Fenfluramine | | | 5 | 49.7 (1.30) | −4.74 | −9.54* | −5.32 | −10.7* |
| Saline | | | 10 | 41.0 (0.92) | 0.22 | 0.54 | 0.92 | 2.24 |
| O-3944 | 20 | 10 | 44.6 (0.84) | −0.78 | −1.75* | −0.91 | −2.04* |
| Saline | | | 10 | 50.9 (1.64) | −0.72 | −1.41 | 0.06 | 0.18 |
| O-3944 | 30 | 10 | 51.8 (1.54) | −1.89 | −3.66* | −2.13 | −4.13* |
| Saline | | | 10 | 48.6 (2.18) | 0.70 | 1.4 | 0.20 | 0.35 |
| O-4309 | 20 | 10 | 53.1 (2.20) | −1.20 | −2.3* | −3.20 | −6.03* |

*pValue <0.05 for compound versus saline control

Example 25

Animal Model Studies for OCD:

Serotonin produces an itch sensation when applied to the human skin and has been suggested to be involved in pruritic diseases. Further research demonstrates that an intraperitoneal (IP) injection of 5-HT into the rostral back of the mouse elicits scratching with the hind paws, which is itch-associated rather than a pain response (Kuraishi, Y., Nagasawa, T., Hayashi, K., Satoh, M. "Scratching Behavior Induced by Pruritogenic but not Algesiogenic Agents in Mice" *Eur. J. Pharmacol.* 1995, 275, 229). The 5-HT action is at least partly mediated by 5-HT$_2$ receptors in the skin, as shown by blocking with specific antagonists (Yamaguchi, T., Nagasawa, T., Satoh, M., Kuraishi, Y. "Itch-associated Response Induced by Intradermal Serotonin Through 5-HT2 Receptors in Mice" *Neurosci. Res.* 1999, 35, 77). The effect of test compounds on itch-associated scratching in the mice may indicate their action on 5-HT receptors, and a study was carried out as an animal model for OCD. The subjects were male Swiss-Webster mice, 4-6 weeks old, weighing 25-45 g. Mice were Mice were injected subcutaneously between the shoulder blades with either 0.1 ml of serotonin, 0.4 mg per ml in 0.15 M saline plus ascorbic acid, 1 mg/ml, or compound 48-80 (the copolymer product of N-methyl-p-methoxyphenethylamine with formaldehyde), 1.0 mg/ml in saline plus ascorbic acid. Test compounds were injected i.p. 5 minutes before the inducer. The cumulative number of scratches with a hind leg was recorded at 5 minute intervals for 30 minutes. One saline injected control and one test animal were tested together in each assay. The results are shown in Table 5.

TABLE 5

| Compound (Treatment 1) | Dose (mg/kg) | Inducer | N | Average Number of Scratches 30 min. after injection (±SEM) | Average Number of Control Scratches 30 min. after injection (±SEM) | Number of Scratches as Percentage of Control |
| --- | --- | --- | --- | --- | --- | --- |
| +/−Fenfluramine | 10 | Serotonin | 5 | 12.8* (8) | 196.2 (59) | 6.5 |
| Fluoxetine | 10 | Serotonin | 10 | 15 (8) | 369 (112) | 4.1 |
| O-3804 | 5 | Serotonin | 5 | 128.4 (62) | 375.6 (161) | 34.2 |
| | 20 | Serotonin | 5 | 12.8* (13) | 583.2 (161) | 2.2 |
| O-3944 | 2 | Serotonin | 5 | 231.6 (149) | 589.4 (217) | 39.3 |
| | 5 | Serotonin | 5 | 113.4* (65) | 560.4 (191) | 20.2 |
| | 30 | 48-80 | 5 | 0* (0) | 670.25 (46) | 0 |
| O-4309 | 2.5 | Serotonin | 5 | 181.4 (91) | 186.2 (104) | 97.4 |
| | 5 | Serotonin | 5 | 89.6 (62) | 504.6 (143) | 17.8 |
| | 10 | Serotonin | 5 | 8.8 (4) | 540 (183) | 1.6 |

The results demonstrate that the number of scratches was decreased when mice were treated with certain compounds of the invention, compared to control animals.

The disclosures of each and every patent, patent application and publication cited herein are hereby incorporated herein by reference in their entirety.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A compound of formula (I):

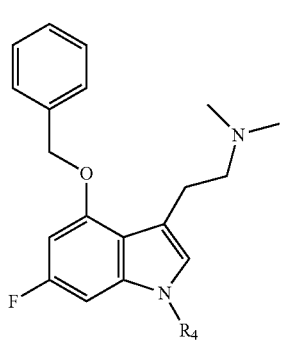

wherein:
R is —CH₃, —CH₂CH₃, —CH₂CH₂CH₃, —CH₂CH₂CH₂CH₃, -cyclopropylmethyl, —CH(CH₃)₂, —SO₂CH₃, or —SO₂CH₂CH₃.

2. A compound of formula (II):

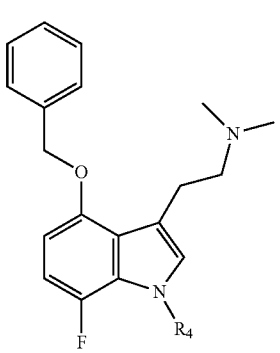

wherein:
R is —CH₃, —CH₂CH₃, —CH₂CH₂CH₃, —CH₂CH₂F, —CH₂CH₂CH₂CH₃, -cyclopropylmethyl, —CH(CH₃)₂, —SO₂CH₃, or —SO₂CH₂CH₃.

3. A compound of the following formula:

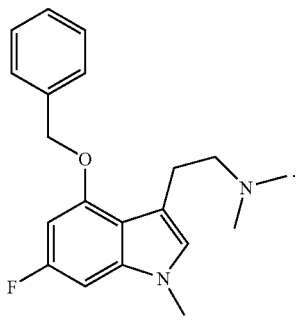

4. A compound of the following formula:

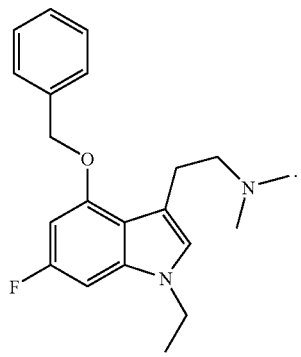

5. A compound of the following formula:

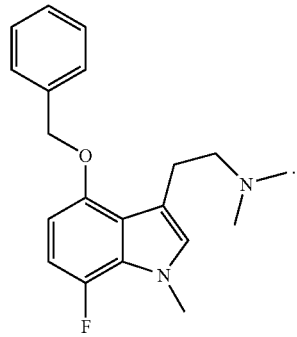

6. The compound of claim 1, wherein the compound is:

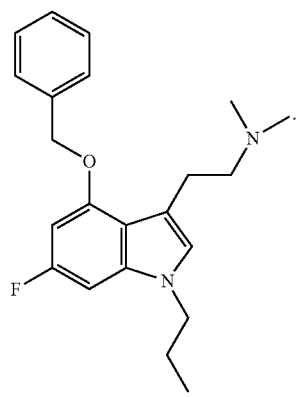

7. The compound of claim 1, wherein the compound is:
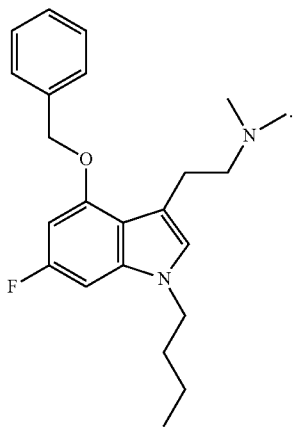
8. The compound of claim 1, wherein the compound is:
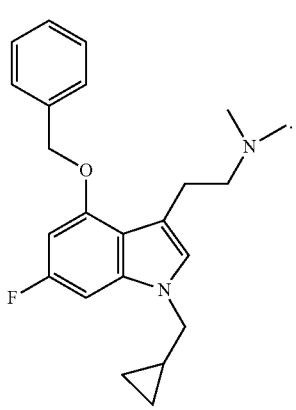
9. The compound of claim 1, wherein the compound is:
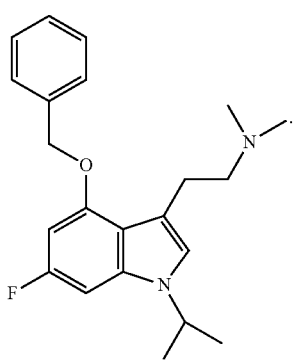
10. The compound of claim 1, wherein the compound is:
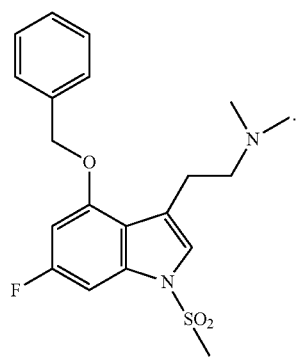
11. The compound of claim 1, wherein the compound is:
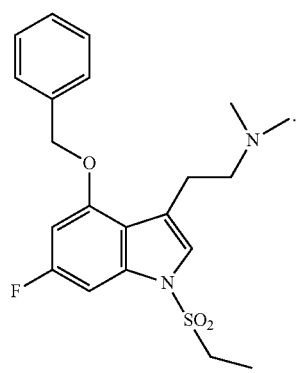
12. The compound of claim 2, wherein the compound is:
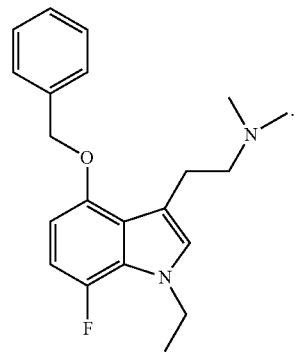

13. The compound of claim 2, wherein the compound is:
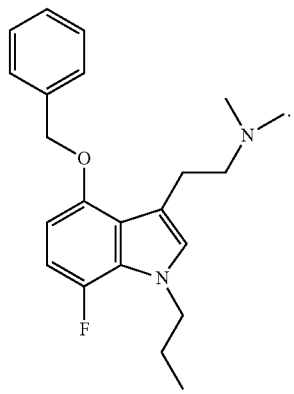
14. The compound of claim 2, wherein the compound is:
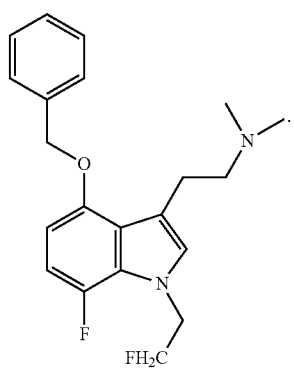
15. The compound of claim 2, wherein the compound is:
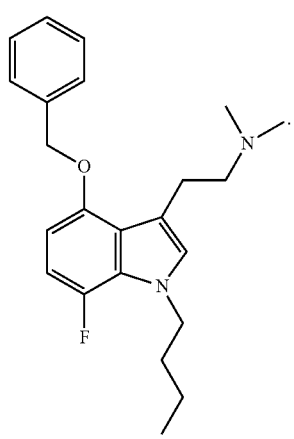
16. The compound of claim 2, wherein the compound is:
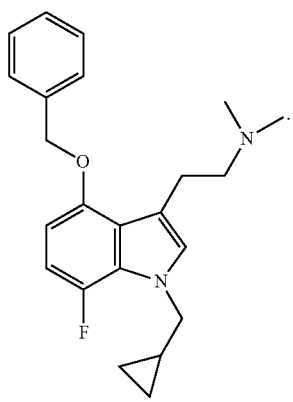
17. The compound of claim 2, wherein the compound is:
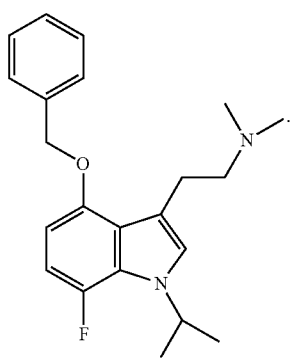
18. The compound of claim 2, wherein the compound is:
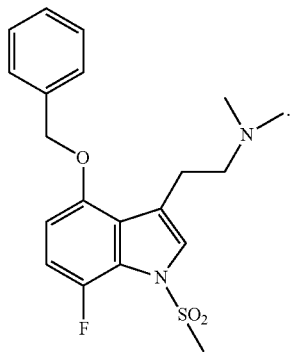

19. The compound of claim 2, wherein the compound is:
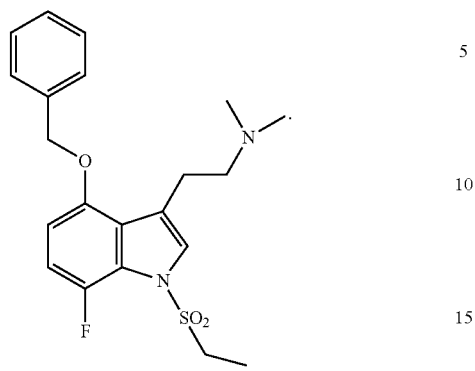
* * * * *